US012390155B2

(12) United States Patent
Rockne et al.

(10) Patent No.: US 12,390,155 B2
(45) Date of Patent: Aug. 19, 2025

(54) PREDICTING WOUND MANAGEMENT TREATMENT RESOURCES USING MACHINE LEARNING

(71) Applicant: MatrixCare, Inc., Bloomington, MN (US)

(72) Inventors: Jessica Rockne, West Jordan, UT (US); Vivek Kumar, Eden Prairie, MN (US); Adhiraj Ganpat Prajapati, St. Paul, MN (US); Robert W. Price, Lockport, IL (US); Kedar Mangesh Kadam, Nova Scotia (CA); Timothy James Heeren, Bloomington, MN (US); Nitin Gandhi, North Liberty, IA (US); Coleen Patrice Danielson, Fergus Falls, MN (US)

(73) Assignee: MatrixCare, Inc., Bloomington, MN (US)

( * ) Notice: Subject to any disclaimer, the term of this patent is extended or adjusted under 35 U.S.C. 154(b) by 450 days.

(21) Appl. No.: 17/562,817

(22) Filed: Dec. 27, 2021

(65) Prior Publication Data
US 2023/0200724 A1 Jun. 29, 2023

(51) Int. Cl.
A61B 5/00 (2006.01)
A61B 5/103 (2006.01)
(Continued)

(52) U.S. Cl.
CPC ............ A61B 5/445 (2013.01); A61B 5/1032 (2013.01); A61B 5/7465 (2013.01);
(Continued)

(58) Field of Classification Search
CPC ..... A61B 5/445; A61B 5/1032; A61B 5/7465; A61B 5/4836; A61B 5/7267;
(Continued)

(56) References Cited

U.S. PATENT DOCUMENTS 11,195,281 B1 12/2021 Schoess et al.
11,348,679 B1* 5/2022 Perry ..................... G16H 40/20
(Continued)

FOREIGN PATENT DOCUMENTS

EP 3499510 A1 6/2019
WO 2020264423 A1 12/2020

OTHER PUBLICATIONS

Mombini et al.: Design Of A Machine Learning System For Prediction Of Chronic Wound Management Decisions, 2020, DOI: 10.1007/978-3-030-64823-7 2 (Year: 2020).
(Continued)

Primary Examiner — Qian Yang
(74) Attorney, Agent, or Firm — Patterson + Sheridan, LLP

(57) ABSTRACT

Certain aspects of the present disclosure provide techniques for predicting wound management treatment resources. This includes determining characteristics of a wound for a patient based on an image of the wound, including detecting the characteristics based on analyzing the image using a first machine learning (ML) model trained to detect wound characteristics from a captured image. The techniques further include predicting at least one of: (i) treatment resources or (ii) a treatment facility for treating the wound, including providing to a second trained ML model characteristics of
(Continued)

the wound, patient medical data for the patient, and treatment facility data describing a plurality of available treatment facilities.

20 Claims, 17 Drawing Sheets

(51) Int. Cl.
*G06T 7/00* (2017.01)
*G16H 50/30* (2018.01)

(52) U.S. Cl.
CPC ........... *G06T 7/0012* (2013.01); *G16H 50/30* (2018.01); *G06T 2207/20081* (2013.01); *G06T 2207/20084* (2013.01); *G06T 2207/30088* (2013.01)

(58) Field of Classification Search
CPC ......... G06T 7/0012; G06T 2207/20081; G06T 2207/20084; G06T 2207/30088; G06T 2207/10024; G06T 2207/10028; G06T 2207/30096; G16H 50/30; G16H 20/10; G16H 80/00; G16H 20/40; G16H 30/40; G16H 40/20; G16H 40/67; G16H 50/20; G16H 50/70
See application file for complete search history.

(56) References Cited

U.S. PATENT DOCUMENTS

| | | |
|---|---|---|
| 2013/0012788 A1 | 1/2013 | Horseman |
| 2013/0085773 A1 | 4/2013 | Yao et al. |
| 2014/0006045 A1 | 1/2014 | Wund, II |
| 2014/0278830 A1 | 9/2014 | Gagne |
| 2016/0012191 A1 | 1/2016 | Kuchipudi et al. |
| 2016/0012192 A1 | 1/2016 | Radhakrishnan et al. |
| 2016/0328525 A1 | 11/2016 | Gross et al. |
| 2017/0061621 A1 | 3/2017 | Wortman |
| 2017/0236281 A1 | 8/2017 | Dacosta |
| 2018/0322941 A1 | 11/2018 | Krishnan et al. |
| 2019/0343429 A1 | 11/2019 | Elhawary et al. |
| 2020/0082941 A1 | 3/2020 | Wang et al. |
| 2020/0126226 A1 | 4/2020 | Adiri et al. |
| 2020/0193597 A1* | 6/2020 | Fan .................... A61B 5/7275 |
| 2020/0202527 A1* | 6/2020 | Choi ........................ G06T 5/73 |
| 2020/0210868 A1* | 7/2020 | Gharat ..................... G06N 5/04 |
| 2020/0211701 A1 | 7/2020 | Martindale et al. |
| 2020/0273548 A1 | 8/2020 | Wolf et al. |
| 2020/0357498 A1 | 11/2020 | Clark |
| 2020/0380675 A1* | 12/2020 | Golden .................. G06T 7/143 |
| 2021/0142890 A1 | 5/2021 | Adiri et al. |
| 2021/0142906 A1 | 5/2021 | Bigdeli |
| 2021/0151140 A1* | 5/2021 | Bates ..................... G06N 20/00 |
| 2021/0290152 A1 | 9/2021 | Vogel |
| 2021/0327540 A1 | 10/2021 | Schobel et al. |
| 2021/0353213 A1 | 11/2021 | Heneghan et al. |
| 2022/0354419 A1 | 11/2022 | Kennedy |

OTHER PUBLICATIONS

Moura et al., Artificial intelligence in the management and treatment of burns: a systematic review, Burns & Trauma, vol. 9, 2021, tkab022, https://doi.org/10.1093/burnst/tkab022 (Year: 2021).

Digital Wound Care, "Swift Skin and Wound: How a Smartphone App Is Revolutionizing Wound Care." Swift, Feb. 12, 2019, https://swiftmedical.com/swift-skin-and-wound-how-a-smartphone-app-is-revolutionizing-wound-care/.

PCT, Notification of Transmittal of The International Search Report and The Written Opinion of The International Searching Authority, or The Declaration for Application PCT/US22/82268 dated Apr. 4, 2023.

PCT, Notification of Transmittal of The International Search Report and The Written Opinion of The International Searching Authority, or The Declaration for Application PCT/US22/81961 dated Mar. 29, 2023.

PCT, Nofication of Transmittal of The International Search Report and The Written Opinion of The International Searching Authority, or The Declaration for PCT/US22/82261 dated Mar. 29, 2023.

International Search Report in International Patent Application No. PCT/US2020/039988 mailed Oct. 14, 2020 (4 pp.).

Dalya Vidyashree et al: "Design of smartphone-based wound assessment system", 2016 International Conference On Automatic Control and Dynamic Optimization Techniques (ICACDOT), IEEE, Sep. 9, 2016 (Sep. 9, 2016), pp. 709-712.

Chen H. et al., "Wound Healing Monitoring by Video Sequence Using Integral Optical Flow", Journal of Applied Spectroscopy, Jul. 2019, pp. 435-442; vol. 86, No. 3, (Russian Original vol. 86, No. 3, May-Jun. 2019); 2019 Springer Science & Business Media, LLC.

Wang L. et al., "Wound Image Analysis System for Diabetics", Advances in Resist Technology and Processing XVI, Mar. 13, 2013; pp. 866924-1 to 866924-14; vol. 8669; US.

Chakraborty C. et al., "Telemedicine Supported Chronic Wound Tissue Prediction Using Classification Approaches", J Med Syst, Jan. 4, 2016; pp. 1-12; vol. 40: 68; Springer Science & Business Media, LLC, New York US.

Treuillet S. et al., "Three-Dimensional Assessment of Skin Wounds Using a Standard Digital Camera", IEEE Transactions On Medical Imaging, May 2009; pp. 752-762; vol. 28, No. 5; IEEE, US.

Yang, S. et al., "Sequential Change of Wound Calculated by Image Analysis Using a Color Patch Method during a Secondary Intention Healing"; PLOS I One, Sep. 20, 2016; pp. 1-15. OI:10.1371/journal.pone.0163092.

Ozturk C. et al., "Measurement of wound healing by image analysis," Biomedical Science Instrumentation; Technical Papers Composing the Proceedings of the 32nd Annual Rocky Mountain Biomedical Symposium and 32nd International ISA Biomedical Sciences Instrumentation Symposium, Apr. 7-9, 1995; pp. 189-193, vol. 31, Instrument Society of America 1995.

West, John B., "Respiratory Physiology", 9th edition published 2012, Lippincott Williams & Wilkins.

International Preliminary Report on Patentability received for PCT Patent Application No. PCT/US2022/081961, mailed on Jul. 11, 2024, 10 pages.

* cited by examiner

PREDICTING WOUND MANAGEMENT TREATMENT RESOURCES USING MACHINE LEARNING

INTRODUCTION

Aspects of the present disclosure relate to artificial intelligence and healthcare, and more specifically, to predicting wound management treatment resources using computer vision and machine learning (ML).

Predicting the necessary resources for treating a patient wound can be very difficult. For example, differing wounds, and patients, can take dramatically different times for treatment and can require very different resources, especially in terms of staffing and equipment. Incorrectly predicting the resources (e.g., including time) necessary to treat a patient's wound can be extremely harmful to the patient, because placing the patient in a healthcare setting that does not include sufficient resources, or moving the patient from one healthcare setting to another because treatment is taking longer than expected, can have a significant negative impact on the patient's treatment. Further, incorrectly predicting the resources necessary to treat a patient's wound can be wasteful. The difficulty in predicting the necessary resources can lead care providers to recommend highly resourced treatment settings (e.g., an in-patient facility), out of an abundance of caution, when the patient might be more suited to a more comfortable and less expensive lower resourced treatment setting (e.g., an out-patient facility). This is both detrimental to the patient, and detrimental to the community at large by taking unnecessary spaces in highly resourced facilities.

SUMMARY

Certain embodiments provide a method. The method includes determining a plurality of characteristics of a wound for a patient based on an image of the wound, including detecting the plurality of characteristics based on analyzing the image using a first machine learning (ML) model trained to detect wound characteristics from a captured image. The method further includes predicting at least one of: (i) treatment resources or (ii) a treatment facility for treating the wound, including: providing to a second trained ML model the plurality of characteristics of the wound, patient medical data for the patient, and treatment facility data describing a plurality of available treatment facilities.

Further embodiments provide an apparatus including a memory, and a hardware processor communicatively coupled to the memory, the hardware processor configured to perform operations. The operations include determining a plurality of characteristics of a wound for a patient based on an image of the wound, including detecting the plurality of characteristics based on analyzing the image using a first ML model trained to detect wound characteristics from a captured image. The operations further include predicting at least one of: (i) treatment resources or (ii) a treatment facility for treating the wound, including providing to a second trained ML model the plurality of characteristics of the wound, patient medical data for the patient, and treatment facility data describing a plurality of available treatment facilities.

Further embodiments provide a non-transitory computer-readable medium including instructions that, when executed by a processor, cause the processor to perform operations. The operations include determining a plurality of characteristics of a wound for a patient based on an image of the wound, including detecting the plurality of characteristics based on analyzing the image using a first ML model trained to detect wound characteristics from a captured image. The operations further include predicting at least one of: (i) treatment resources or (ii) a treatment facility for treating the wound, including providing to a second trained ML model the plurality of characteristics of the wound, patient medical data for the patient, and treatment facility data describing a plurality of available treatment facilities.

The following description and the related drawings set forth in detail certain illustrative features of one or more embodiments.

DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
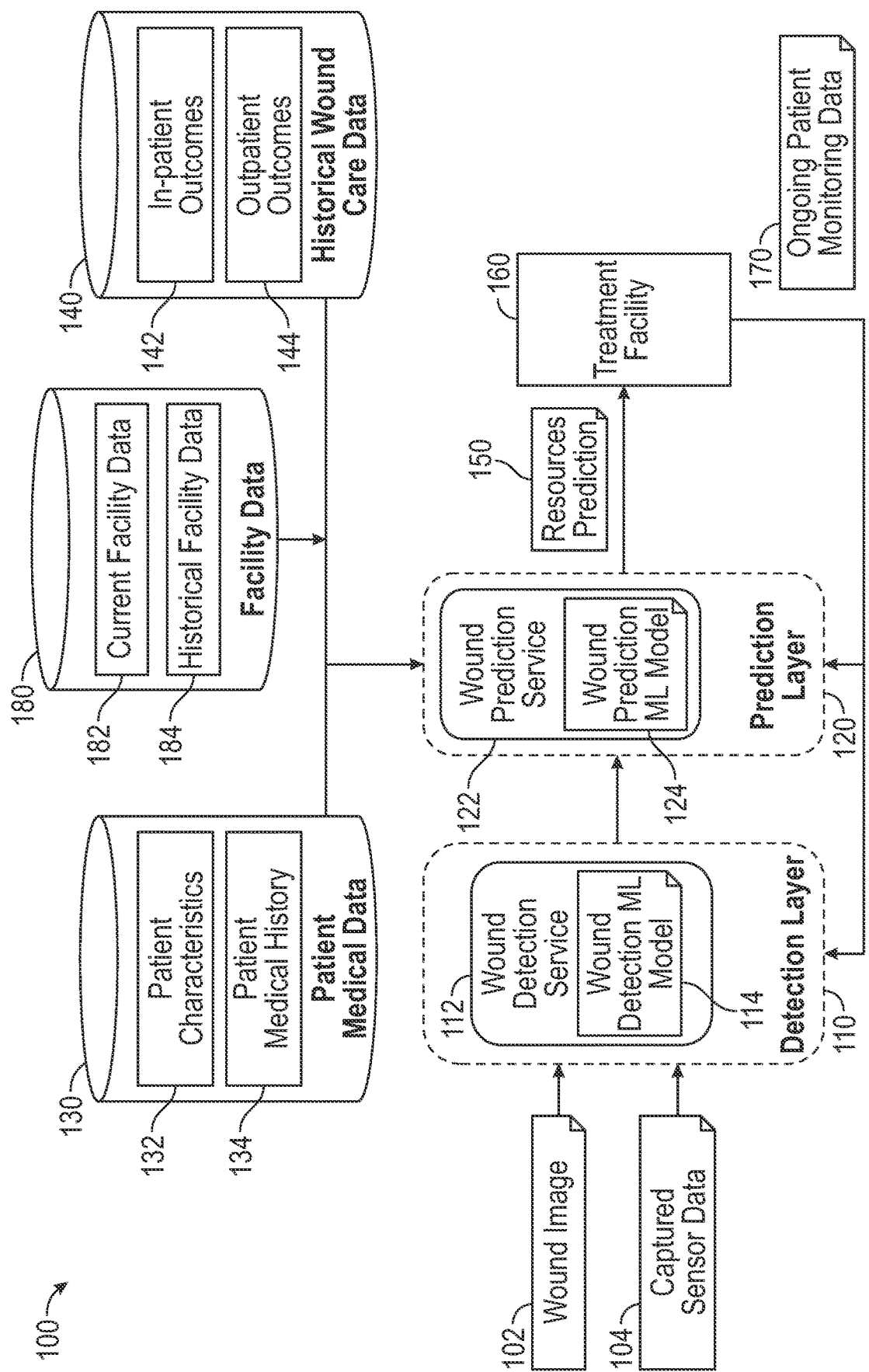
FIG. 1 depicts a computing environment for wound management and treatment using computer vision and ML, according to one embodiment.

Aspects of the present disclosure provide apparatuses, methods, processing systems, and computer-readable mediums for improved wound management and treatment using computer vision and ML. As discussed above, predicting the treatment resources necessary for a patient wound is very challenging, and incorrect predictions have significant drawbacks. For example, an incorrect prediction can lead to a patient being treated at a facility lacking necessary resources, or being moved between facilities for treatment. Further, the inaccuracy of prediction can lead care providers to recommend highly resources facilities for patients, when lower resourced facilities might be more appropriate, tying up valuable resources for other patients and increasing the expense for treatment.

In aspects described herein, necessary resources for treating a patient wound can instead be predicted automatically using a trained ML model, based on a captured image of the wound and/or other captured sensor data. For example, a patient or care provider can capture an image of a patient wound. Computer vision techniques (e.g., a suitable ML model, as discussed further below) can be used to analyze the image and detect various characteristics of the wound from the image.

A suitable ML model (e.g., a deep learning neural network (DNN)) can be trained to predict necessary treatment resources based on the detected wound characteristics and additional information about the patient. For example, the ML model can use patient characteristics (e.g., demographic information, medication information, and assessment information) and patient medical history (e.g., prior medical conditions and treatments for the patient), along with the detected wound characteristics, to predict necessary treatment resources for the wound. The necessary treatment resources can outline an expected treatment time, expected staffing needed, expected equipment needed (e.g., testing and treatment equipment), and other useful information. A care provider, or the patient them self, can then use these predicted resources to select a suitable course of treatment for the wound. Further, the predicted treatment resources can be used to ensure that appropriate supplies are available for treatment (e.g., interfacing with a facility or supplier inventory system), and that appropriate staffing is available (e.g., interfacing with a staffing scheduling system).

Further, in various aspects, the ML model can be trained to predict a preferred treatment facility for the patient (e.g., as part of predicting necessary treatment resources). Selecting a treatment facility, both a particular facility and a type of facility (e.g., in-patient or out-patient) is also an extremely challenging problem. And selecting an inappropriate facility can lead to poor patient outcomes (e.g., if the facility lacks necessary resources or experience) and unnecessary expense (e.g., if the facility includes extra resources not needed for treatment). The ML model can use detected wound characteristics, patient characteristics, and facility characteristics (e.g., current and historical facility data) to predict a preferred treatment facility for the patient. This can include selecting among available in-patient facilities, selecting between in-patient and out-patient treatment, or selecting among out-patient treatment options (e.g., selecting an appropriate level of oversight and assistance for out-patient treatment), among other options.

In an embodiment, the ML model can be trained to predict treatment resources (e.g., including predicting a preferred facility) using data about historical wound care incidents. For example, the ML model can receive data about prior patient wounds, including characteristics of the relevant patient and wound, the care plan used, the facility used, and the resolution of the treatment. As noted above, this data can be used to train the ML model to predict treatment resources for a newly identified wound, based on characteristics of the wound (e.g., detected from an image using computer vision techniques), the patient, and available facility options.

Aspects described herein provide significant advantages. For example, predicting resources needed to treat a patient wound using a trained ML model provides for an accurate prediction while minimizing the needed computational resources for the prediction and shifting the computational burden from prediction time (e.g., when near real-time response may be needed) to an earlier training time (e.g., when resources can be easily dedicated to the training). In an embodiment, necessary treatment resources could be predicted using a specific rubric or algorithm with pre-defined rules, but this may be computationally expensive, because a very large number of rules are needed and parsing and following the rules is computationally expensive. Further, this computationally expensive analysis is done at the time the resource are predicted, when a rapid response is likely to be needed (e.g., so that the patient can be treated quickly).

Predicting resources needed for treating a patient wound automatically using a trained ML model, by contrast, is significantly less computationally expensive at the time the prediction generated. For example, the ML model can be trained up-front during a training phase, when rapid response is not necessary and computational resources are readily available. The trained ML model can then be used to rapidly, and computationally relatively cheaply, predict treatment resources for the patient.

As another example, predicting resources needed for treating a patient wound automatically using a trained ML model, based on a captured image of the wound or other captured sensor data, provides for a more accurate and well-defined result. In an embodiment, a care provider could manually predict the expected resources needed to treat the wound. But this leaves the risk of human error, and a lack of certainty in the accuracy of the prediction. Predicting the needed resources using a trained ML model can both lessen the risk of human error, and provide more certainty in the level of accuracy of the prediction. Further, the prediction can itself be reviewed and refined by a care provider. This provides a starting point for the care provider with a more certain level of accuracy, and reduces the burden on the care provider to generate the prediction themselves.

Example Computing Environment

FIG. 1 depicts a computing environment 100 for wound management and treatment using computer vision and ML, according to one embodiment. In an embodiment, a captured wound image 102 is provided to a detection layer 110. For example, a patient may have a wound (e.g., bedsores, sutures, abrasions, lesions, or any other wound) that is detectable using an image capture device. The patient, a healthcare, a caretaker, or any other person can capture an image of the wound using the image capture device (e.g., a digital camera). For example, a patient or healthcare professional can use a camera integrated into a smartphone or tablet computer to capture the wound image 102, and can use a suitable secure application to provide the image to the detection layer 110. This is merely one example, and any suitable image capture device can be used by any suitable person, or entity, to capture the wound image 102. For example, an automated sensor could be used to automatically trigger image capture of the wound image 102 (e.g., during a medical examination). Further, the image capture device can operate outside the visual spectrum (e.g., an infrared sensor, an x-ray sensor, or any other suitable sensor).

In an embodiment, the captured wound image 102 is provided to the detection layer 110 using a suitable communication network. For example, the wound image 102 can be captured using a camera in a computing device (e.g., a smartphone or tablet computer camera) and can be transferred to the detection layer using the computing device. The computing device can use any suitable communication network, including the Internet, a wide area network, a local area network, or a cellular network, and can use any suitable wired or wireless communication technique (e.g., WiFi or cellular communication). This is merely one example, and the wound image 102 can be captured by a camera and provided to a computing device using any suitable technique (e.g., using storage medium or through a wired or wireless transmission from the camera to the computing device).

The detection layer 110 includes a wound detection service 112, which includes a wound detection ML model 114. In an embodiment, the wound detection service 112 facilitates transformation of incoming patient data (e.g., wound image 102). For example, as discussed below with regard to FIG. 2, the wound detection service 112 can be a computer software service implemented in a suitable controller (e.g., the prediction controller 200 illustrated in FIG. 2) or combination of controllers. In an embodiment the detection layer 110, and the wound detection service 112, can be implemented using any suitable combination of physical compute systems, cloud compute nodes and storage locations, or any other suitable implementation. For example, the detection layer 110 could be implemented using a server or cluster of servers. As another example, the detection layer 110 can be implemented using a combination of compute nodes and storage locations in a suitable cloud environment. For example, one or more of the components of the detection layer 110 can be implemented using a public cloud, a private cloud, a hybrid cloud, or any other suitable implementation.

As one example, the wound detection service 112 can facilitate computer vision analysis of the wound image 102. In this example, the wound detection ML model 114 can be a suitable computer vision ML model (e.g., a DNN, support vector machine (SVM), or any other suitable ML model). In an embodiment, the wound detection ML model 114 can be trained to receive the wound image 102, and to recognize or detect various characteristics of the wound depicted in the image. These can include exterior characteristics (e.g., size and color), interior characteristics (e.g., size, color, and depth), location, and any other suitable characteristics. This is discussed further below with regard to FIGS. 4-5 and 8.

In an embodiment, the wound image 102 is merely one example of patient data that can be analyzed using the detection layer 110 (e.g., using the wound detection service 112 and the wound detection ML model 114). For example, captured sensor data 104 can also be provided to the detection layer 110. In an embodiment, the captured sensor data 104 includes data captured by sensors used during treatment or rehabilitation of a patient (e.g., captured during treatment of a wound). For example, the captured sensor data 104 can include data from negative pressure wound therapy devices, oxygen and intubation devices, monitored pressure and drainage devices, or any other suitable devices.

In an embodiment, the wound detection service 112 can further facilitate analysis of the captured sensor data 104. For example, the wound detection service 112 can use a wound detection ML model 114 to detect and identify characteristics of the patient's wound based on the captured sensor data. In an embodiment, the wound detection ML model 114 can be any suitable ML model (e.g., a DNN, or a non-neural-network ML model) trained to detect and identify characteristics of the patient's wound.

Further, in an embodiment, the wound detection ML model 114 can include multiple ML models trained to detect wound characteristics from different data. For example, one ML model could be trained to use computer vision techniques to identify wound characteristics from the wound image 102, another ML model could be trained to detect wound characteristics based on sensor data from a wound therapy device, and another ML model could be trained to detect wound characteristics based on sensor data from monitored pressure devices. This is merely an example, and the wound detection ML model could instead be trained to use data from multiple sources (e.g., the wound image 102 and captured sensor data 104), together, to detect and identify characteristics of the patient's wound.

In an embodiment, the detection layer 110 provides wound detection data to a prediction layer 120. For example, the wound detection service 112 can use the wound detection ML model 114 to detect characteristics of a patient wound, using the wound image 102, the captured sensor data 104, or both. The detection layer 110 can provide these wound characteristics to the prediction layer 120.

The prediction layer 120 includes a wound prediction service 122 and a wound prediction ML model 124. In an embodiment, the wound prediction service 122 facilitates prediction of treatment and rehabilitation information for the patient wound. For example, the wound prediction service 122 can use the wound prediction ML model 124 to determine a resources prediction 150 (e.g., a prediction of the resources needed for treatment). This is discussed further below with regard to FIGS. 7A-B.

As discussed below with regard to FIG. 2, the wound prediction service 122 can be a computer software service implemented in a suitable controller (e.g., the prediction controller 200 illustrated in FIG. 2) or combination of controllers. In an embodiment the prediction layer 120, and the wound prediction service 122, can be implemented using any suitable combination of physical compute systems, cloud compute nodes and storage locations, or any other suitable implementation. For example, the prediction layer 120 could be implemented using a server or cluster of servers. As another example, the prediction layer 120 can be implemented using a combination of compute nodes and storage locations in a suitable cloud environment. For example, one or more of the components of the prediction layer 120 can be implemented using a public cloud, a private cloud, a hybrid cloud, or any other suitable implementation.

As discussed above, the prediction layer 120 uses the detected characteristics of the patient wound (e.g., the output from the detection layer 110) to predict the treatment and rehabilitation information for the patient wound. In an embodiment, however, the wound characteristics detected by the detection layer 110 are not sufficient to allow the prediction layer 120 to accurately predict the treatment and rehabilitation information for the patient wound. For example, merely identifying the characteristics of the wound may not be sufficient to identify a suitable treatment plan for the patient, and may not be sufficient to identify a predicted treatment duration and suitable treatment facility for the patient.

In an embodiment, the prediction layer 120 can further receive, and use, patient medical data 130 and historical wound care data 140. For example, the patient medical data 130 can include patient characteristics 132 and patient medical history 134. In an embodiment, the patient characteristics 132 can include patient demographics (e.g., age, height, weight), patient medications (e.g., a listing of medications for the patient), patient assessment data (e.g., intake assessment data, discharge assessment data, activities of daily living (ADL) assessment data), or any other suitable patient characteristics. This is discussed further below with regard to FIG. 9. In an embodiment, the patient medical history 134 can include medical condition data (e.g., diagnosis, onset, treatment, and resolution) for any prior medical conditions. This is discussed further below with regard to FIG. 10.

In an embodiment, the historical wound care data 140 can include data about in-patient outcomes 142 and out-patient outcomes 144, for various patients and various wounds. For example, the historical wound care data 140 can include wound characteristics for a wound (e.g., exterior characteristics, interior characteristics, and location), patient characteristics for the patient with the wound (e.g., demographics, medications, assessments, and medical history), care plan history for the wound (e.g., treatments used), facility characteristics for treatment of the wound (e.g., type of facility, staffing at the facility, and available resources at the facility), resolution data (e.g., time and resources used in treatment, and result of the treatment), and any other suitable historical wound care data. In an embodiment, the patient medical data 130 provides data about the particular patient with the wound, while the historical wound care data 140 provides data about historical treatments and resolutions for a variety of wounds and patients. Further, in an embodiment, the historical wound care data 140 has had any personally identifying patient information removed.

In an embodiment, the patient medical data 130 and the historical wound care data 140 are provided to the prediction layer 120 using a suitable communication network. For example, the patient medical data 130 and the historical wound care data 140 can be stored in one or more suitable electronic databases (e.g., a relational database, a graph database, or any other suitable database) or other electronic repositories (e.g., a cloud storage location, an on-premises network storage location, or any other suitable electronic repository). The patient medical data 130 and the historical wound care data 140 can be provided from the respective electronic repositories to the prediction layer 120 using any suitable communication network, including the Internet, a wide area network, a local area network, or a cellular network, and can use any suitable wired or wireless communication technique (e.g., WiFi or cellular communication).

In an embodiment, the prediction layer 120 can further receive, and use, facility data 180. For example, the facility data can include current facility data 182 and historical facility data 184. In an embodiment, the current facility data 182 can include staffing data (e.g., available physicians, nurses, technicians), equipment data, availability data, and any other suitable data. This is discussed further below with regard to FIG. 12A. Further, the historical facility data can include historical staffing data, historical outcome data, historical availability data, and any other suitable. This is discussed further below with regard to FIG. 12B.

As discussed above, in an embodiment, the wound prediction service 122 uses the wound prediction ML model 124 to predict treatment and rehabilitation information for the patient wound. For example, the wound prediction ML model 124 can be a suitable supervised ML model (e.g., a DNN) trained to generate a resources prediction 150 (e.g., a prediction of resources needed for treatment) for the patient wound from a combination of wound characteristics for the particular wound at issue (e.g., output from the detection layer 110), patient medical data 130, historical wound care data 140, and facility data. This is discussed further below with regard to FIG. 3. For example, the wound prediction ML model 124 can be selected based on initial analysis of the input data (e.g., the wound characteristics, patient medical data 130, historical wound care data 140, and facility data). In an embodiment, a basic technique can be initially selected (e.g., logistic regression), data can be converted to a numerical format, and based on initial analysis data transformation and ML techniques can be chosen. This is merely an example, and any suitable supervised, or unsupervised, techniques can be used.

For example, the wound prediction ML model 124 can predict treatment resources expected to be needed for the wound, including an expected time for treatment of the wound. This is one example of a resources prediction 150. As another example, the wound prediction ML model 124 can predict a preferred treatment facility for the patient (e.g., a particular in-patient treatment facility, or out-patient treatment). This is another example of a resources prediction 150. Further, in an embodiment, the wound prediction ML model 124 can predict a treatment facility based on a facility score, rather than the facility data 180. For example, an additional ML model (e.g., a facility evaluation ML model) can use the current facility data 182 and the facility history data 184 to generate a facility score for available facilities. The wound prediction ML model 124 can use this facility score to predict the treatment facility. This is discussed below in relation to FIG. 7B. This is merely an example, however, and the wound prediction ML model 124 can instead, or in addition, use the facility data 180 directly without creation of an intermediate treatment facility score.

In an embodiment, the resources prediction 150 can be provided to a treatment facility 160. The treatment facility 160 can be any suitable in-patient or out-patient treatment facility. Further, in an embodiment, the resources prediction 150 can be provided directly to the patient or to the patient's medical care provider. This is discussed further below with regard to FIGS. 14A-B. In an embodiment, the resources prediction 150 is provided to any, or all of the treatment facility, the patient, and the care provider using a suitable communication network. For example, the resources prediction 150 can be provided from the prediction layer 120 to the destination (e.g., treatment facility, patient, or care provider) using any suitable communication network, including the Internet, a wide area network, a local area network, or a cellular network, and can use any suitable wired or wireless communication technique (e.g., WiFi or cellular communication).

In an embodiment, the resources prediction 150 is used to treat the patient. For example, the resources prediction 150 can be a prediction of the time needed to treat the patient's wound. Alternatively, or in addition, the resources prediction 150 can be a prediction of a preferred treatment facility. In either instance care providers, or the patient them self, can use the resources prediction 150 to treat the patient.

In an embodiment, the treatment of the wound can be monitored, and ongoing patient monitoring data 170 can be gathered. For example, repeated images of the wound can be captured, other sensor data can be provided, care providers can provide assessment data, and any other suitable data can be gathered. Further, in an embodiment, captured data can be maintained in suitable repository (e.g., an electronic database) and used for training (e.g., training the ML model). This data, and all training data, can be stripped of any personally identifying patient information.

In an embodiment, this ongoing patient monitoring data 170 can be provided to the detection layer 110, the prediction layer 120, or both, and used to refine the prediction of available resources 150. For example, captured images or other captured sensor data can be provided to the detection layer 110 and analyzed in the same way as the wound image 102 and the captured sensor data 104 (e.g., to identify ongoing wound characteristics as the wound is treated). As another example, updated patient medical data can be provided to the prediction layer 120 and analyzed in the same way as the patient medical data 130.

Further, in an embodiment, the ongoing patient monitoring data 170 can be used to continuously train the wound prediction ML model 124. For example, the wound prediction ML model 124 can determine, from the ongoing patient monitoring data 170 (e.g., from detected wound characteristics of additional captured images of the wound as it is treated), whether the wound treatment has required the expected resources. As one example, the color or depth of the wound may change during treatment, indicating progress in healing, over a period of time. The wound prediction service 122 can use the prior resources prediction, and the result of the care as indicated by the ongoing patient monitoring data (e.g., the duration and resources used to achieve the demonstrated level of healing), as additional training data to further train the wound prediction ML model 124 to make a resources prediction for the patient (e.g., to adjust the predicted treatment time or to predict a different preferred treatment location).

Figure 2:
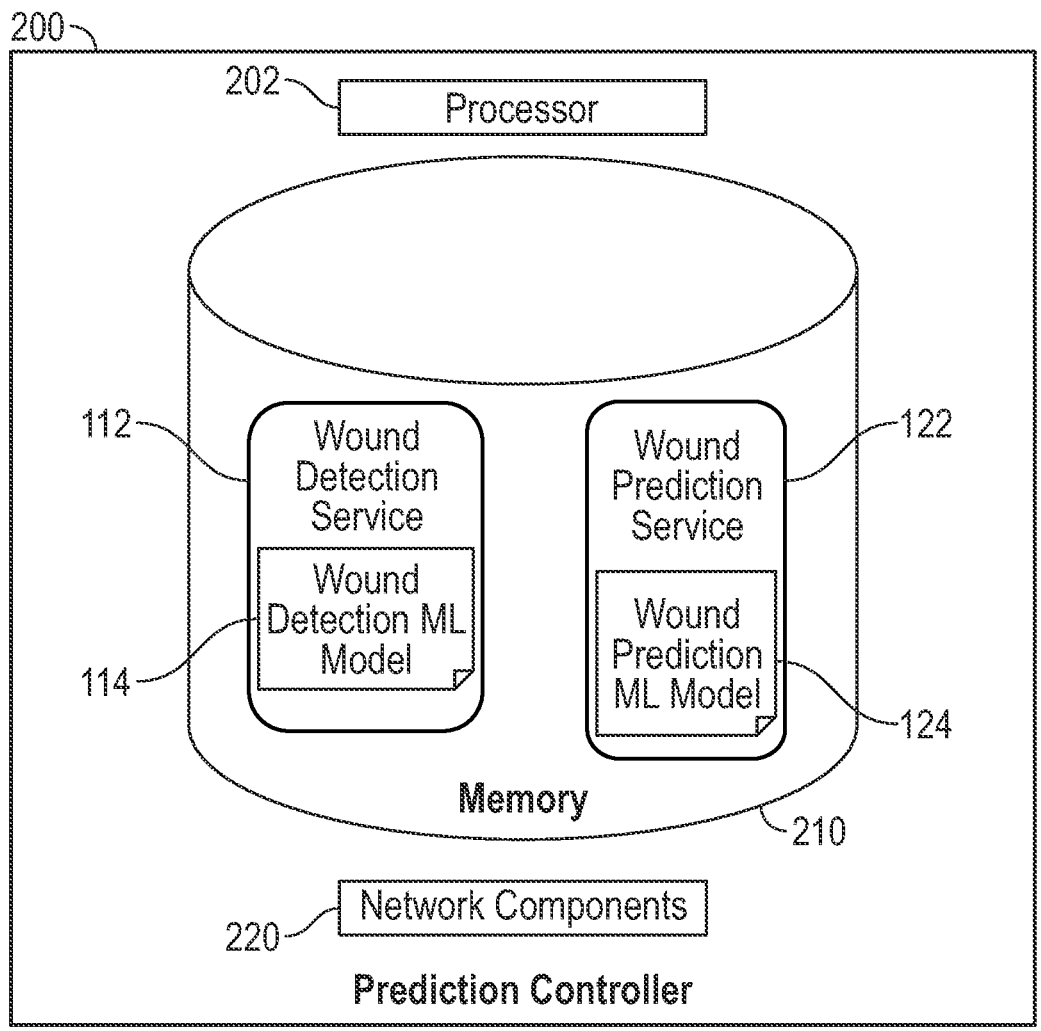
FIG. 2 depicts a block diagram for a prediction controller for wound management and treatment using computer vision and ML, according to one embodiment.

FIG. 2 depicts a block diagram for a prediction controller 200 for wound management and treatment using computer vision and ML, according to one embodiment. The controller 200 includes a processor 202, a memory 210, and network components 220. The memory 210 may take the form of any non-transitory computer-readable medium. The processor 202 generally retrieves and executes programming instructions stored in the memory 210. The processor 202 is representative of a single central processing unit (CPU), multiple CPUs, a single CPU having multiple processing cores, graphics processing units (GPUs) having multiple execution paths, and the like.

The network components 220 include the components necessary for the controller 200 to interface with a suitable communication network (e.g., a communication network interconnecting various components of the computing environment 100 illustrated in FIG. 1, or interconnecting the computing environment 100 with other computing systems). For example, the network components 220 can include wired, WiFi, or cellular network interface components and associated software. Although the memory 210 is shown as a single entity, the memory 210 may include one or more memory devices having blocks of memory associated with physical addresses, such as random access memory (RAM), read only memory (ROM), flash memory, or other types of volatile and/or non-volatile memory.

The memory 210 generally includes program code for performing various functions related to use of the prediction controller 200. The program code is generally described as various functional "applications" or "modules" within the memory 210, although alternate implementations may have different functions and/or combinations of functions. Within the memory 210, the wound detection service 112 facilitates detecting wound characteristics from captured sensor data (e.g., captured images and other captured sensor data), using the wound detection ML model 114. This is discussed further below with regard to FIGS. 4-6. The wound prediction service 122 facilitates predicting treatment and rehabilitation information for a wound, using the wound prediction ML model 124. This is discussed further below with regard to FIGS. 3 and 7A-B.

While the controller 200 is illustrated as a single entity, in an embodiment, the various components can be implemented using any suitable combination of physical compute systems, cloud compute nodes and storage locations, or any other suitable implementation. For example, the controller 200 could be implemented using a server or cluster of servers. As another example, the controller 200 can be implemented using a combination of compute nodes and storage locations in a suitable cloud environment. For example, one or more of the components of the controller 200 can be implemented using a public cloud, a private cloud, a hybrid cloud, or any other suitable implementation.

Although FIG. 2 depicts the wound detection service 112, the wound prediction service 122, the wound detection ML model 114, and the wound prediction ML model 124, as being mutually co-located in memory 210, that representation is also merely provided as an illustration for clarity. More generally, the controller 200 may include one or more computing platforms, such as computer servers for example, which may be co-located, or may form an interactively linked but distributed system, such as a cloud-based system, for instance. As a result, processor 202 and memory 210 may correspond to distributed processor and memory resources within the computing environment 100. Thus, it is to be understood that any, or all, of the wound detection service 112, the wound prediction service 122, the wound detection ML model 114, and the wound prediction ML model 124 may be stored remotely from one another within the distributed memory resources of the computing environment 100.

Figure 3:
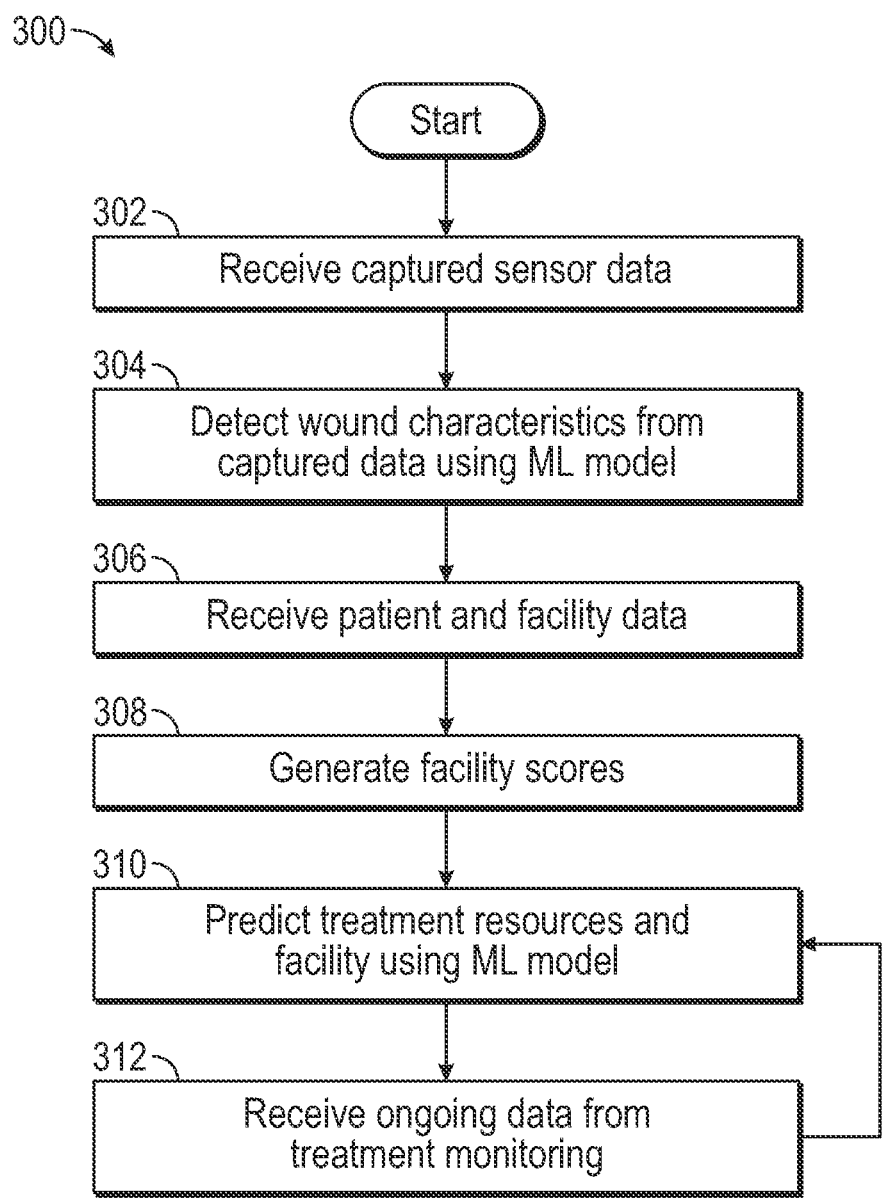
FIG. 3 is a flowchart illustrating predicting wound management treatment resources using computer vision and ML, according to one embodiment.

FIG. 3 is a flowchart 300 illustrating predicting wound management treatment resources using computer vision and ML, according to one embodiment. At block 302 a wound detection service (e.g., the wound detection service 112 illustrated in FIGS. 1-2) receives captured sensor data relating to a patient wound. For example, as discussed above in relation to FIG. 1, in an embodiment the wound detection service can receive a captured wound image (e.g., the wound image 102 illustrated in FIG. 1), captured sensor data (e.g., the captured sensor data 104 illustrated in FIG. 1), or both.

At block 304, the wound detection service detects wound characteristics from the captured data using an ML model. For example, the wound detection service can use a captured image, sensor data, or both to detect exterior characteristics (e.g., size and color), interior characteristics (e.g., size, color, and depth), location, and any other suitable characteristics of the wound. As discussed above in relation to the wound detection ML model 114 illustrated in FIG. 1, the wound detection service can use any suitable ML model, or combination of ML models, to detect wound characteristics from the captured sensor data. This is discussed further below with regard to FIGS. 4-6.

At block 306, a prediction service (e.g., the wound prediction service 122 illustrated in FIGS. 1-2) receives patient and facility data. For example, the prediction service can receive the patient medical data 130 and the facility data 180 illustrated in FIG. 1. This can include patient characteristics (e.g., patient demographics, patient medications, patient assessment data, or any other suitable patient characteristics), patient medical history (e.g., medical condition data for any prior medical conditions), and current and historical facility data. This is discussed further below with regard to FIGS. 9-10 and 12A-B.

In an embodiment, the prediction service can further receive the historical wound care data 140 illustrated in FIG. 1. This can include historical data about in-patient outcomes and out-patient outcomes, for various patients and various wounds. This is discussed further below with regard to FIG. 11. In an embodiment, the prediction service uses the historical wound care data for ongoing training of the prediction ML model. Alternatively, the prediction service does not receive the historical wound care data. In this example, the historical wound care data is used to train the prediction ML model (e.g., as discussed below in relation to FIG. 13 but is not used for inference (e.g., for prediction).

At block 308, the prediction service generates facility scores. For example, the prediction service can use the received facility data (e.g., current and historical facility data) to generate suitability scores for treating the patient's wound at any available facilities. The facility data can, for example, include a listing of available facilities to treat the patient's wound (e.g., including in-patient and out-patient options), current facility information for these facilities, and historical facility information for these facilities. In an embodiment, the prediction service uses a suitable ML model (e.g., a facility evaluation ML model) to generate facility scores for the available facilities. This is discussed further below with regard to FIG. 7B.

At block 310, the prediction service predicts treatment resources needed to treat the wound, a preferred treatment facility for treating the wound, or both, using one or more ML models. For example, the prediction service can use the wound prediction ML model 124 illustrated in FIGS. 1-2 to predict needed treatment resources. This can include needed staffing, needed equipment, and expected time needed. As another example, the prediction service can use the wound prediction ML model 124 to predict a suitable treatment facility for the patient (e.g., selected from among available facilities). As discussed above, in one embodiment the prediction ML model 124 receives facility scores (e.g., generated by an additional ML model at block 308) describing the suitability of various facilities, and uses the facility scores to predict a suitable treatment facility. Alternatively, or in addition, the prediction ML model 124 uses the facility data directly (e.g., without requiring intermediate facility scores). This is discussed further below with regard to FIGS. 7A-B.

As illustrated the prediction ML model uses all of the wound characteristics, the patient medical data, the historical wound care data, and the facility data, to predict the treatment resources and facility. But this is merely an example. Alternatively, or in addition, the prediction ML model can use any subset of this data (e.g., where some of this data is unavailable for a given patient wound). For example, the prediction ML model can use the wound characteristics and patient medical data, without historical wound care data, or wound characteristics and historical wound care data, without patient medical data. In an embodiment this may result in a slight loss of accuracy in predicting treatment resources and facility, but the predicted treatment resources and facility are still significantly improved over prior techniques (e.g., manual prediction).

In an embodiment, the prediction service can further identify a prophylactic treatment task for the wound (e.g., a treatment task intended to quickly prevent further disease or issues with the wound). For example, the prediction service can use the wound characteristics, the patient medical data, including but not limited to specific health related data associated with one or more patients, such as age, weight, medical conditions, demographics, or other such data, or both to identify a high priority treatment task (e.g. a medication, bandaging, or another medical procedure) needed for the wound (e.g., bedsores, sutures, abrasions, lesions, or any other wound). As one example, a wound could be identified as requiring immediate medical treatment (e.g., bandaging, a surgical procedure, a particular medication, or any other suitable treatment), to prevent further disease or issues with the wound. Thus, for example, a bedsore, suture, abrasion, or lesion could be identified as requiring immediate medication, immediate bandaging, or another immediate medical procedure. The prediction service can transmit an alert (e.g., an e-mail, SMS message, telephone call, or another form of electronic message) describing the treatment task to a care provider for the patient (e.g., via a care facility for the patient) or to the patient themselves. The care provider or patient can then treat the wound using the treatment task. In an embodiment, the prediction service can identify this treatment task prior to completing the prediction of the treatment resources and facility. For example, the prediction service can identify a high priority treatment task while predicting the treatment resources or facility, and can transmit the alert prior to completing the prediction of the treatment resources or facility. In an embodiment this allows for a rapid alert for the treatment task, without waiting for complete prediction of the treatment resources or facility.

At block 312, the prediction service receives ongoing data form treatment monitoring. For example, the prediction service can receive additional sensor data (e.g., additional images) captured during treatment and rehabilitation of the patient wound. This data can be captured at a treatment facility (e.g., an in-patient or out-patient facility), by a suitable medical professional or by the patient them self. In an embodiment, the prediction service can use the ongoing data to further refine the prediction of the treatment resources or facility.

Example of Detecting Wound Characteristics from a Captured Image

Figure 4:
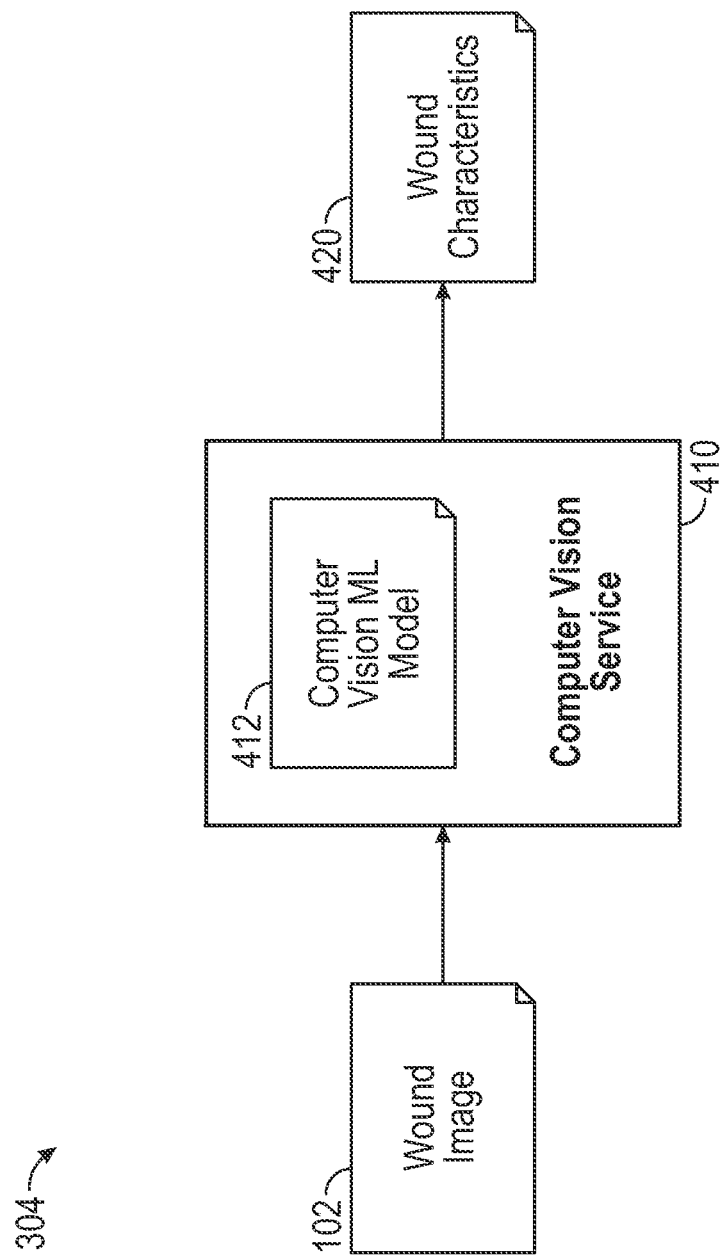
FIG. 4 illustrates detecting wound characteristics from a captured image using computer vision, according to one embodiment.

FIG. 4 illustrates detecting wound characteristics from a captured image using computer vision, according to one embodiment. In an embodiment, FIG. 4 provides one example of detecting wound characteristics from captured data using an ML model, discussed above in relation to block 304 illustrated in FIG. 3. A wound image 102 (e.g., as discussed above in relation to FIG. 1) is provided to a computer vision service 410 and a computer vision ML model 412. In an embodiment, the wound image 102 is an image of the patient wound captured using any suitable image capture device (e.g., a camera, a medical imaging device, or any other suitable image capture device).

In an embodiment, the computer vision service 410 is one example of a wound detection service 112, and the computer vision ML model 412 is one example of a wound detection ML model 114, both illustrated in FIGS. 1-2. As discussed above, in an embodiment the wound detection service 112 can detect wound characteristics from a variety of captured sensor data, including a captured image or captured sensor data from treatment devices, using the wound detection ML model. The computer vision service 410 detects wound characteristics 420 from the wound image 102 using the computer vision ML model 412.

In an embodiment, the computer vision ML model 412 can be any suitable ML model. For example, a non-neural network ML model can be used (e.g., a SVM). This can use any suitable object detection, recognition, or identification technique. As another example, a neural network ML model can be used (e.g., a CNN), and can use any suitable object detection, recognition, or identification technique.

As discussed above, the wound characteristics 420 can include any suitable wound characteristics. These can include exterior characteristics (e.g., size and color), interior characteristics (e.g., size, color, and depth), location, and any other suitable characteristics. This is discussed further below with regard to FIG. 8.

Figure 5:
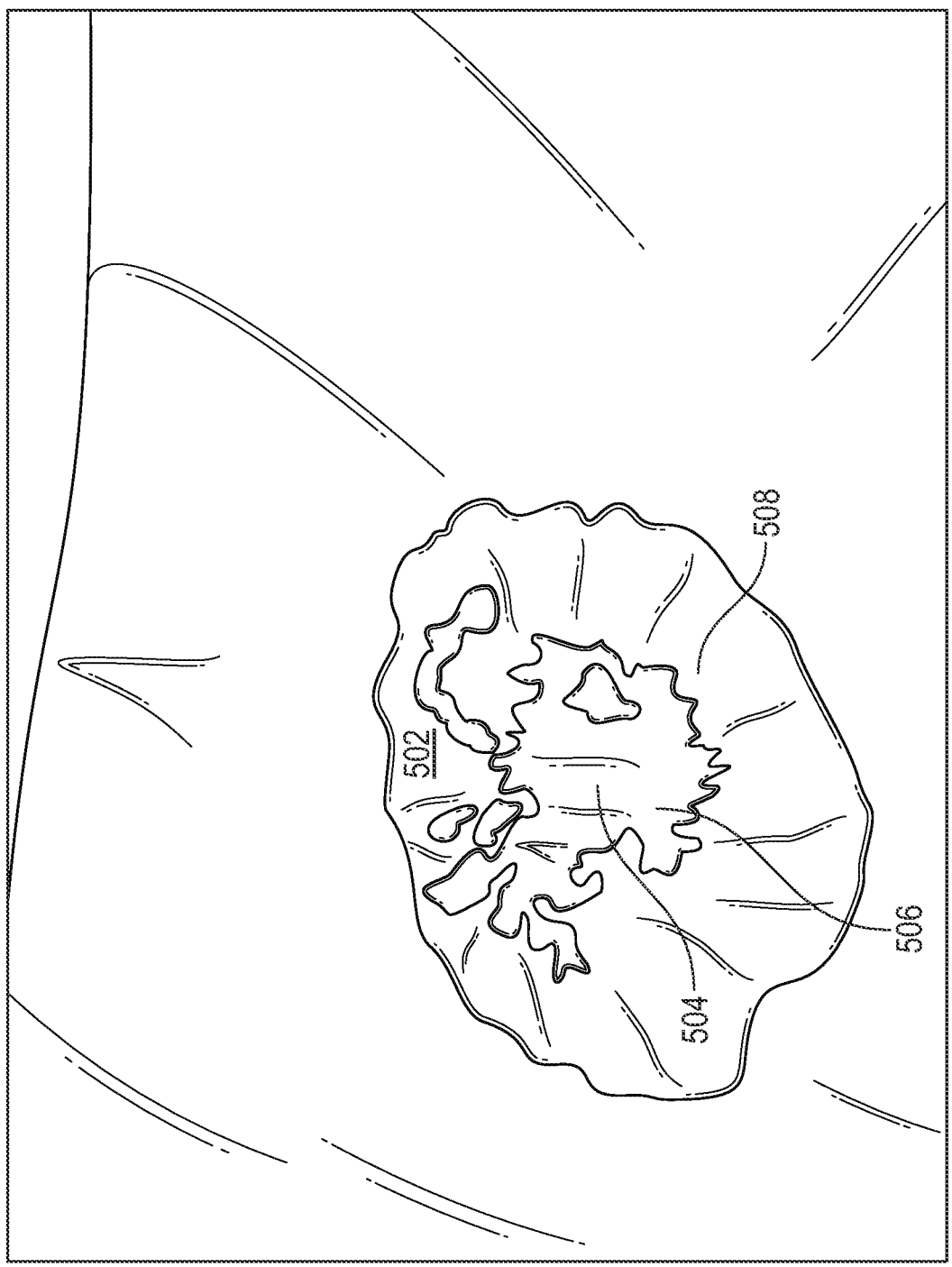
FIG. 5 depicts an example of detecting wound characteristics from a captured image using computer vision, according to one embodiment.

FIG. 5 depicts an example of detecting wound characteristics from a captured image using computer vision, according to one embodiment. In an embodiment, a captured image depicts a wound on a patient. As discussed above, a suitable wound detection service (e.g., the computer vision service 410 illustrated in FIG. 4) detects characteristics of the wound from the image, using a suitable wound detection ML model (e.g., the computer vision ML model 412 illustrated in FIG. 4). For example, the wound detection service can detect an exterior size 502 and an exterior color 508. As another example, the wound detection service can detect an interior size and color 506, and a depth 504

Example of Training a Computer Vision ML Model

Figure 6:
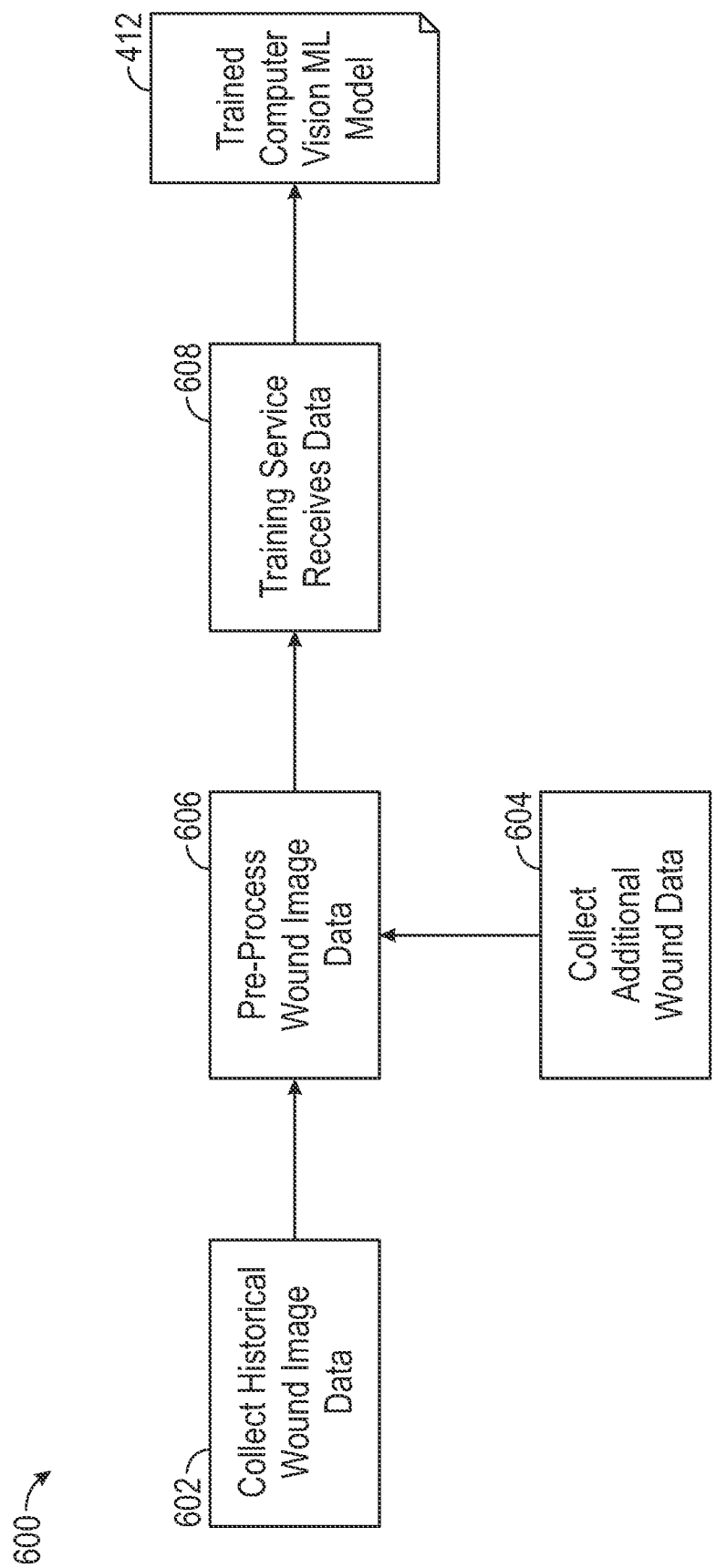
FIG. 6 is a flowchart illustrating training a computer vision ML model for wound management and treatment, according to one embodiment.

FIG. 6 is a flowchart 600 illustrating training a computer vision ML model for wound management and treatment, according to one embodiment. This is merely an example, and in an embodiment a suitable unsupervised technique could be used (e.g., without requiring training). At block 602, a training service (e.g., a human administrator or a software or hardware service) collects historical wound image data. For example, a wound detection service (e.g., the wound detection service 112 illustrated in FIGS. 1 and 2) can be configured to act as the training service and collect previously captured images of patient wounds (e.g., gathered over time). This is merely an example, and any suitable software or hardware service can be used (e.g., a wound detection training service).

At block 606, the training service (or other suitable service) pre-processes the collected historical wound image data. For example, the training service can create feature vectors reflecting the values of various features, for each collected wound image. At block 608, the training service receives the feature vectors and uses them to train a trained computer vision ML model 412 (e.g., the computer vision model 412 illustrated in FIG. 4).

In an embodiment, at block 604 the training service also collects additional wound data (e.g., data generated from in-person evaluation of the wound). At block 606, the training service can also pre-process this additional wound data. For example, the feature vectors corresponding to the historical wound image data can be further annotated using the additional wound data. Alternatively, or in addition, additional feature vectors corresponding to the additional wound data can be created. At block 608, the training service uses the pre-processed additional wound data during training to generate the trained computer vision ML model 412.

In an embodiment, the pre-processing and training can be done as batch training. In this embodiment, all data is pre-processed at once (e.g., all historical wound image data and additional wound data), and provided to the training service at block 608. Alternatively, the pre-processing and training can be done in a streaming manner. In this embodiment, the data is streaming, and is continuously pre-processed and provided to the training service. For example, it can be desirable to take a streaming approach for scalability. The set of training data may be very large, so it may be desirable to pre-process the data, and provide it to the training service, in a streaming manner (e.g., to avoid computation and storage limitations). Further, in an embodiment, a federated learning approach could be used in which multiple healthcare entities contribute to training a shared model.

Example of Predicting Wound Management Treatment Resources

Figure 7A:
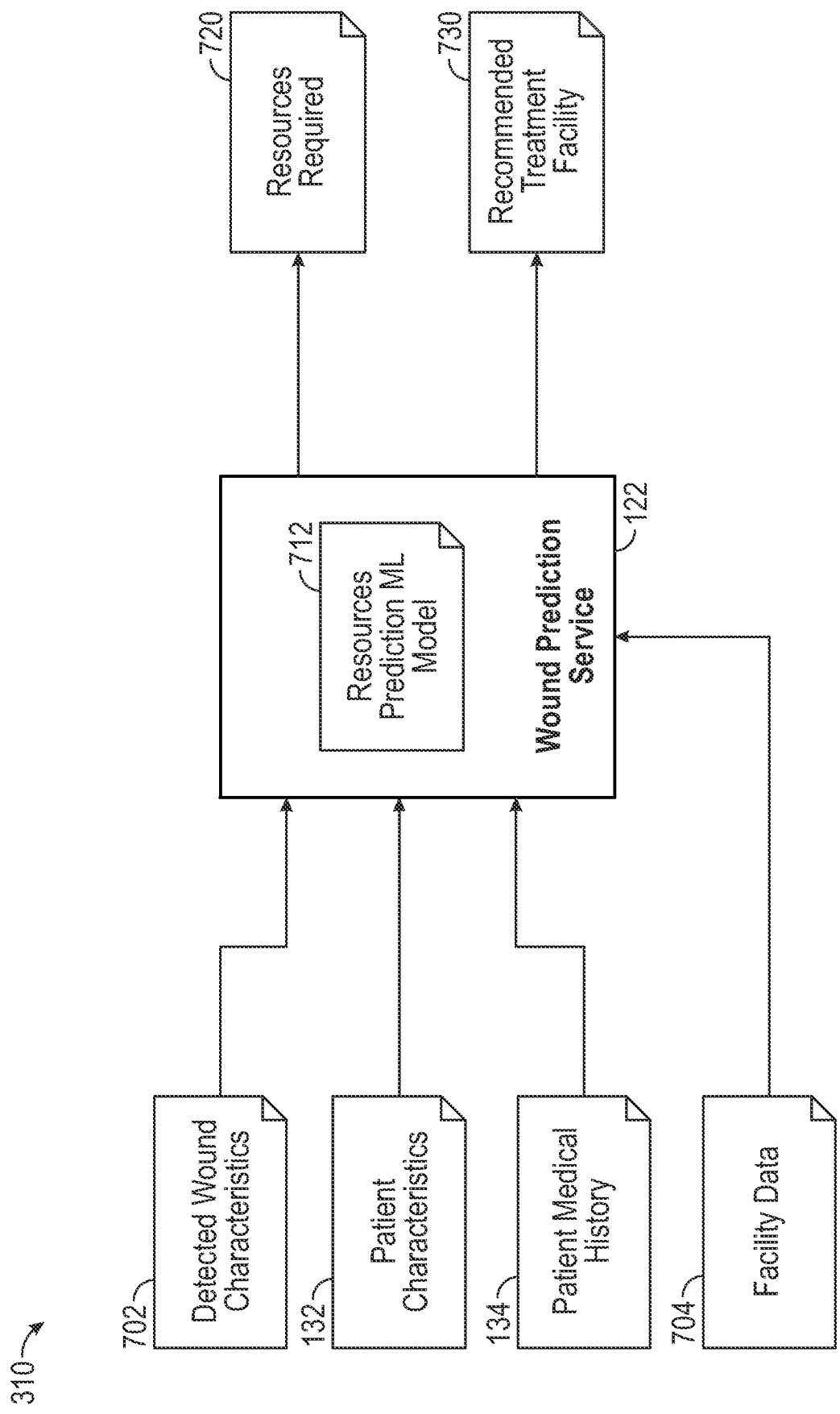
FIG. 7A depicts predicting wound management treatment resources using an ML model, according to one embodiment.

FIG. 7A depicts predicting wound management treatment resources using an ML model. In an embodiment, FIG. 7A corresponds with block 310 illustrated in FIG. 3, above. A wound prediction service 122, as discussed above in relation to FIGS. 1-2, is associated with a resources prediction ML model 712. In an embodiment, the resources prediction ML model 712 is one example of a wound prediction ML model (e.g., one example of the wound prediction ML model 124 illustrated in FIGS. 1-2). For example, as illustrated the wound prediction service 122 uses the resources prediction model 712 to predict resources required for treatment of the wound 720 (e.g., time, staffing, equipment) and a recommended treatment facility 730.

In an embodiment, the wound prediction service 122 uses multiple types of data to predict the resources required 720 and recommended treatment facility 730, using the resources prediction ML model 712. For example, the wound prediction service 122 can use detected wound characteristics 702. In an embodiment, the detected wound characteristics 702 are generated by a wound detection service (e.g., the wound detection service 112 illustrated in FIGS. 1-2) using a wound detection ML model (e.g., the wound detection ML model 114 illustrated in FIGS. 1-2) by detecting wound characteristics from captured data (e.g., a wound image 102, captured sensor data 104, or both). For example, as illustrated in FIG. 4, a computer vision service 410 can use a computer vision ML model 412 to detect wound characteristics 420 from a wound image 102. As discussed below in relation to FIG. 8, in an embodiment the detected wound characteristics 702 can include exterior characteristics (e.g., size, color), interior characteristics (e.g., size, color, depth), location, and any other suitable characteristics.

In addition, the wound prediction service 122 can use patient characteristics 132 (e.g., as discussed above in relation to FIG. 1) to predict the resources required 720 and recommended treatment facility 730, using the resources prediction ML model 712. As discussed below in relation to FIG. 9, the patient characteristics 132 can include patient demographics (e.g., age, height, weight), patient medications (e.g., a listing of medications for the patient), patient assessment data (e.g., intake assessment data, discharge assessment data, activities of daily living (ADL) assessment data), or any other suitable patient characteristics.

Further, the wound prediction service 122 can use a patient medical history 134 (e.g., as discussed above in relation to FIG. 1) to predict the resources required 720 and recommended treatment facility 730, using the resources prediction ML model 712. As discussed below in relation to FIG. 10, the patient medical history 134 can include medical condition data (e.g., diagnosis, onset, treatment, and resolution) for any prior medical conditions.

The wound prediction service 122 can further use historical wound care data (e.g., as discussed above in relation to FIG. 1) to predict the resources required 720 and recommended treatment facility 730, using the resources prediction ML model 712. As discussed below in relation to FIG. 11, the historical wound care data can include wound characteristics for a wound (e.g., exterior characteristics, interior characteristics, and location), patient characteristics for the patient with the wound (e.g., demographics, medications, assessments, and medical history), care plan history for the wound (e.g., treatments used), facility characteristics for treatment of the wound (e.g., type of facility, staffing at the facility, and available resources at the facility), resolution data (e.g., time and resources used in treatment, and result of the treatment), and any other suitable historical wound care data. As discussed above in relation to FIG. 1, in an embodiment the patient characteristics 132 and patient medical history 134 provide data about the particular patient with the wound, while the historical wound care data provides data about historical treatments and resolutions for a variety of wounds and patients.

In an embodiment, the wound prediction service 122 uses the historical wound care data for ongoing training of the resources prediction ML model 712. For example, because training the resources prediction ML model 712 may be computationally expensive, the wound prediction service can train the resources prediction ML model 712 at suitable intervals (e.g., hourly, daily, weekly) or based on triggering events (e.g., after a threshold number of new observations are received, upon request from an administrator, or at any other suitable interval). Alternatively, the wound prediction service 122 does not receive the historical wound care data. In this example, the historical wound care data 140 is used to train the resources prediction ML model (e.g., as discussed below in relation to FIG. 13) but is not used for inference (e.g., for prediction of the resources required 720 and recommended treatment facility 730).

The wound prediction service 122 can further use facility data 704 (e.g., to predict the recommended treatment facility 730). In one embodiment, the facility data includes current facility data (e.g., staffing data, equipment data, and availability data), as described below with regard to FIG. 12A, and historical facility data (e.g., facility history data, historical staffing data, historical outcome data, and historical availability data), as described below with regard to FIG. 12B. In this embodiment, the wound prediction service uses the resources prediction ML model 712 to predict the recommended treatment facility 730 based on the current and historical facility data. For example, the wound prediction service can identify potential capacity issues at available facilities, potential staffing issues, potential resource issues, and any other suitable potential issues.

Alternatively, or in addition, the facility data 704 includes facility scores. For example, as discussed further below with regard to FIG. 7B, a software service (e.g., a facility evaluation service) can use an additional ML model (e.g., a facility evaluation ML model) to generate facility suitability scores for available facilities. In an embodiment, these facility suitability scores reflect the suitability of the available facilities to treat patient wounds generally, based on both current resources and equipment available and historical outcomes and availability. In this embodiment, the resources prediction ML model 712 uses these facility scores, instead of or in addition to using current and historical facility data directly, to predict the recommended treatment facility 730.

In an embodiment, the resources required 720 include a description of the predicted resources required to treat the patient's wound. For example, the resources required 720 can include an expected treatment time (e.g., in days). In an embodiment, this expected treatment time can be conditional based on treatment resources used (e.g., based on facility, equipment, and medication used). The resources required 720 can further include expected staffing needed, expected equipment needed (e.g., testing or treatment equipment), expected medication needed, and any other suitable information.

The recommended treatment facility 730, in an embodiment, describes a treatment facility recommended to be used to treat the patient's wound. For example, as discussed above, the wound prediction service can use facility data 704, along with patient and wound characteristics, to predict a preferred treatment facility among available facilities. This can include selecting among various available in-patient facilities, selecting a suitable out-patient facility option (e.g., at home care with suitable monitoring and assistance), or selecting any suitable facility option.

Figure 7B:
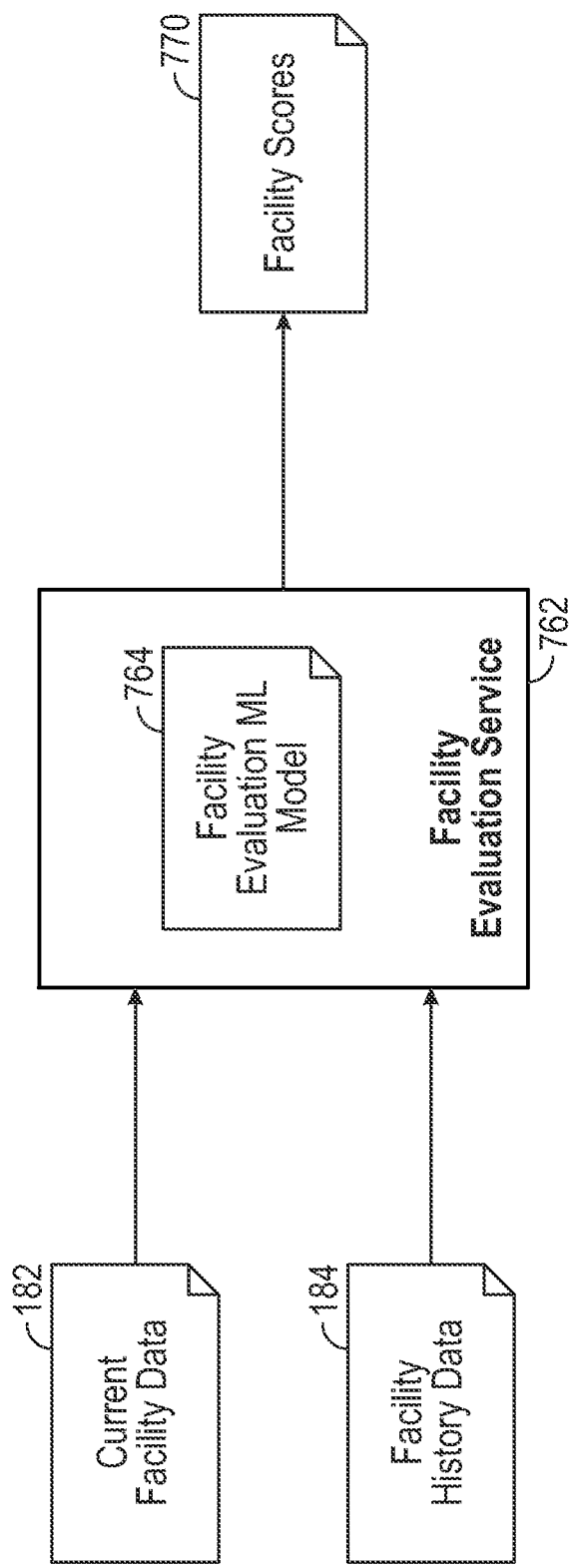
FIG. 7B depicts generating facility scores using an ML model, according to one embodiment.

FIG. 7B depicts generating facility scores using an ML model, according to one embodiment. A facility evaluation service 762 receives current facility data 182 and facility history data 184. In an embodiment, the current facility data includes staffing (e.g., physicians, nurses, technicians) data, equipment data, availability data, and any other suitable data for facilities. This is discussed further below with regard to FIG. 12A. The facility history data 184 includes historical staffing data, historical outcome data, historical availability data, and any other suitable facility history data. This is discussed further below with regard to FIG. 12B.

In an embodiment, the facility evaluation service 762 uses a facility evaluation ML model 764 to generate facility scores 770 from the current facility data 182 and the facility history data 184. For example, the facility evaluation ML model 764 can be any suitable ML model, including a neural network based model (e.g., a DNN) or a non-neural-network based model. The facility evaluation ML model 764 can be trained to use current and historical facility data to generate a suitability score for a given facility.

For example, the facility evaluation ML model 764 can be trained using suitable feature vectors describing current and historical facility characteristics, along with patient wound care outcomes given those characteristics. The trained facility evaluation ML model 764 can then generate facility scores 770 (e.g., suitability scores) for a given collection of facilities using current and historical data for those facilities. In an embodiment, these facility scores reflect the general suitability of available facilities for patient wound care (e.g., without considering the characteristics of the particular patient and the particular wound). A prediction ML model (e.g., the resources prediction ML model 712 illustrated in FIG. 7A) then combines the facility scores 770 with data reflecting patient and wound characteristics to predict a preferred treatment facility. But this is merely one example.

Example Wound and Patient Characteristics

Figure 8:
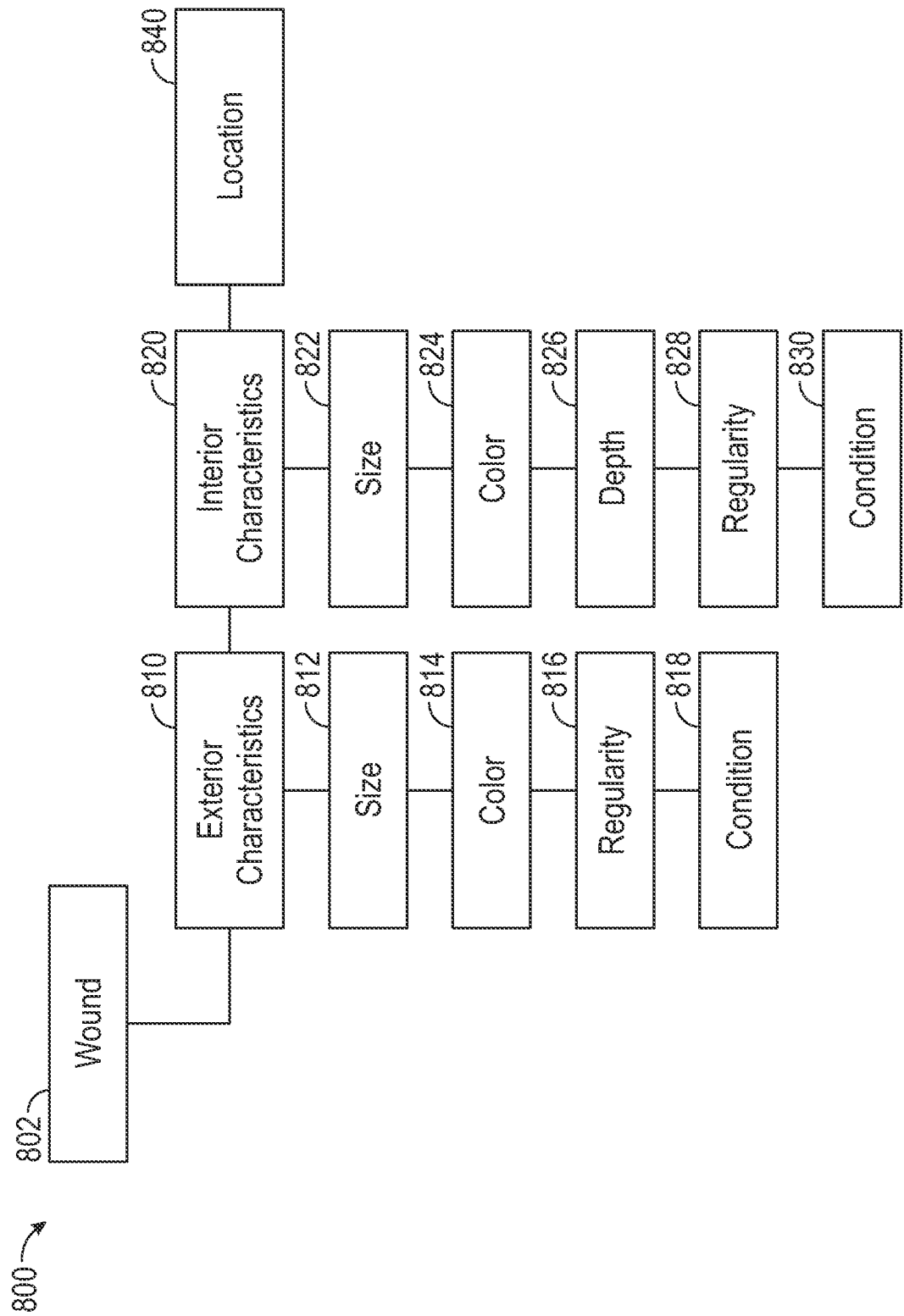
FIG. 8 depicts wound characteristics for use in predicting wound care resources using an ML model, according to one embodiment.

FIG. 8 depicts wound characteristics 800 for use in predicting wound care resources using an ML model, according to one embodiment. In an embodiment, the wound characteristics 800 provide examples for the detected wound characteristics 702, illustrated in FIG. 7A and generated using a suitable wound detection ML model to detect characteristics from captured wound data (e.g., a captured wound image). For example, the wound characteristics 800 can include one or more wounds 802.

In an embodiment, each wound 802 includes exterior characteristics 810. The exterior characteristics 810 include size 812. For example, the size 812 can describe the exterior size of the wound 802 (e.g., the size of an area surrounding an open area of the wound or surrounding a more severely injured portion of the wound). In an embodiment, the size 812 can be described in area (e.g., mm$^2$), dimensions, perimeter circumference, or using any other suitable technique. For example, the size 812 can be expressed as a function describing the exterior size of the wound.

The exterior characteristics 810 can further include a color 814. For example, the color 814 can describe a color of the exterior portion of the wound. The color 814 can be an average color over the exterior area, a most extreme color over the exterior area (e.g., a darkest color, lightest color, color including the largest fraction of a particular shade, etc.), or any other suitable color. Further, the color 814 can be expressed using a numerical value, a tuple (e.g., a red, green, blue (RGB) value), a textual label, or using any other suitable technique.

In an embodiment, the exterior characteristics can further include a regularity 816 (e.g., a regularity of the shape of the wound), and a condition 818 (e.g., a condition of the exterior of the wound). For example, the condition 818 can describe whether the wound is dry or weeping, whether it is sutured or stapled, or any other suitable condition. These are merely examples, and the exterior characteristics 810 can include any suitable characteristics.

In an embodiment, the wound 802 further includes interior characteristics 820. The interior characteristics 820 include a size 822. For example, the size 812 can describe the interior size of the wound (e.g., the size of an open area of the wound or of a more severely injured portion of the wound). In an embodiment, the size 822 can be described in area (e.g., mm$^2$), dimensions, perimeter circumference, or using any other suitable technique. For example, the size 822 can be expressed as a function describing the interior size of the wound.

The interior characteristics 820 can further include a color 824. For example, the color 824 can describe a color of the interior portion of the wound. The color 824 can be an average color over the interior area, a most extreme color over the interior area (e.g., a darkest color, lightest color, color including the largest fraction of a particular shade, etc.), or any other suitable color. Further, the color 824 can be expressed using a numerical value, a tuple (e.g., a red, green, blue (RGB) value), a textual label, or using any other suitable technique.

The interior characteristics 820 can further include a depth 826. For example, the depth 826 can describe a depth of the wound. This can include a tissue depth for an open, or closed, wound, and can be expressed using a measurement (e.g., mm), relative to a surface portion of the skin, using a label, or using any other suitable technique. These are merely examples, and the interior characteristics 820 can include any suitable characteristics.

In an embodiment, the interior characteristics can further include a regularity 828 (e.g., a regularity of the shape of the wound), and a condition 830 (e.g., a condition of the interior of the wound). For example, the condition 830 can describe whether the wound is dry or weeping, whether it is sutured or stapled, or any other suitable condition.

In an embodiment, the wound 802 further includes a location 840. For example, the location 840 can describe the location of the wound on the patient's body. In an embodiment, the location 840 can be described relative to a portion of the patient's body, using a measurement system, or using any other suitable technique. The exterior characteristics 810, interior characteristics 820, and location 840 are merely examples, and the wound 802 can include any suitable characteristics, organized in any suitable manner.

Figure 9:
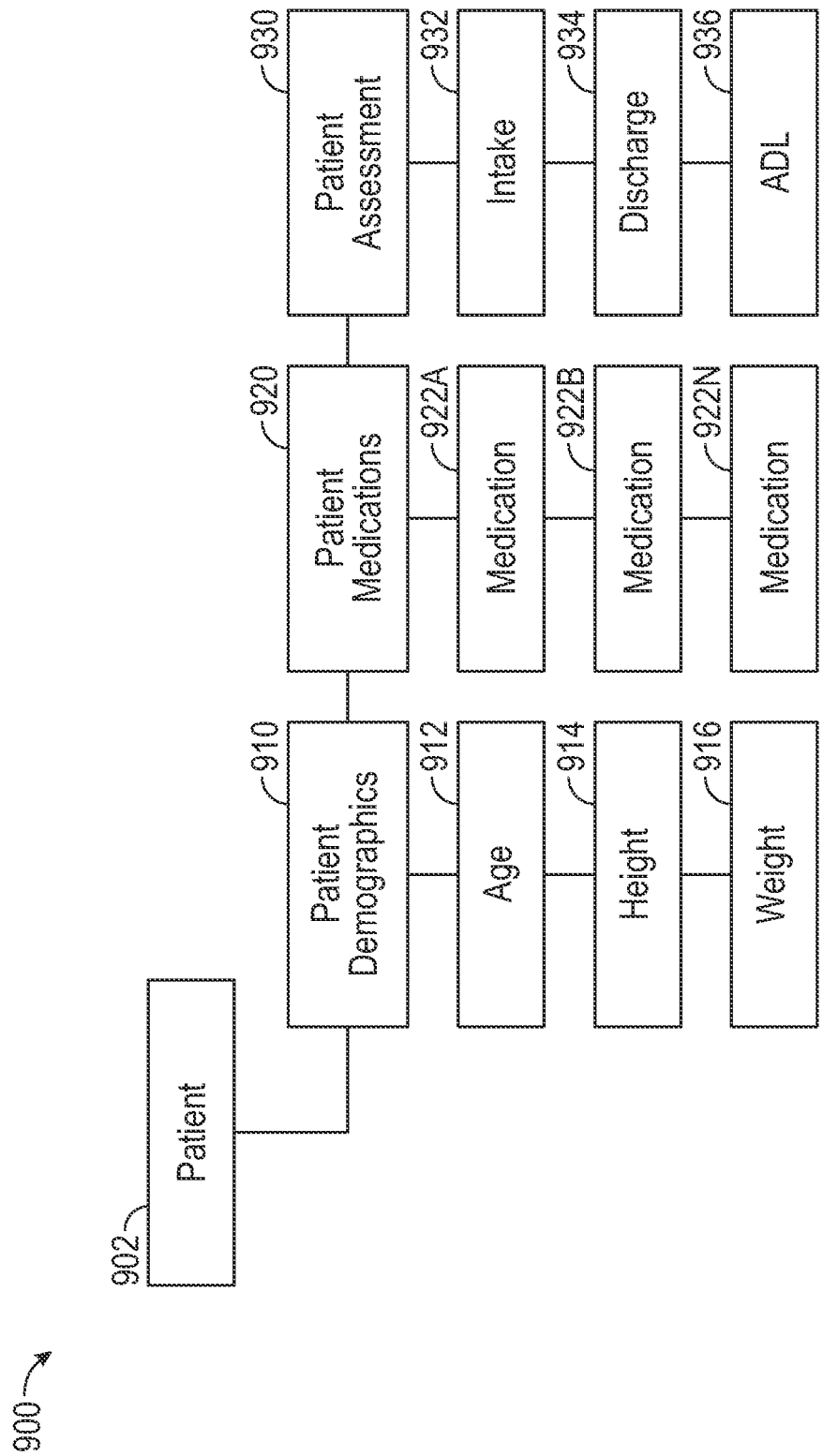
FIG. 9 depicts patient characteristics for use in predicting wound care resources using an ML model, according to one embodiment.

FIG. 9 depicts patient characteristics 900 for use in predicting wound care resources using an ML model, according to one embodiment. In an embodiment, the wound characteristics 900 provide examples for the patient characteristics 132, described above in relation to FIG. 1. A patient 902 includes patient demographics 910. For example, the patient demographics 910 can include age 912, height 914, and weight 916. These are merely examples, and the patient demographics 910 can include any suitable characteristics.

The patient 902 can further include patient medications 920. In an embodiment, the patient medications 920 include one or more medications 922A-N. These are merely examples, and the patient medications 920 can include any suitable data.

Further, the patient 902 can include one or more patient assessments 930 (e.g., a patient assessment 930 corresponding to each healthcare facility to which the patient has been admitted). In an embodiment, the patient assessment 930 includes an intake assessment 932. For example, an intake assessment can be performed for the patient upon intake to a healthcare facility (e.g., performed by a suitable healthcare professional, using a suitable automated assessment system, or both). The intake assessment can be memorialized as the intake assessment 932.

In an embodiment, the patient assessment 930 further includes a discharge assessment 934. For example, a discharge assessment can be performed for the patient upon discharge from a healthcare facility (e.g., performed by a suitable healthcare professional, using a suitable automated assessment system, or both). The discharge assessment can be memorialized as the discharge assessment 934.

The patient assessment 930 can further include an activities of daily living (ADL) assessment 936. For example, the ADL assessment can memorialize the patient's ability to dress, feed, ambulate, toilet, and perform their own hygiene. The ADL assessment can be memorialized as the ADL assessment 936. These are merely examples, and the patient assessment 930 can include any suitable data. Further, the patient demographics 910, patient medications 920, and patient assessment 930 are merely examples. The patient 902 can include any suitable patient data, organized in any suitable fashion.

Figure 10:
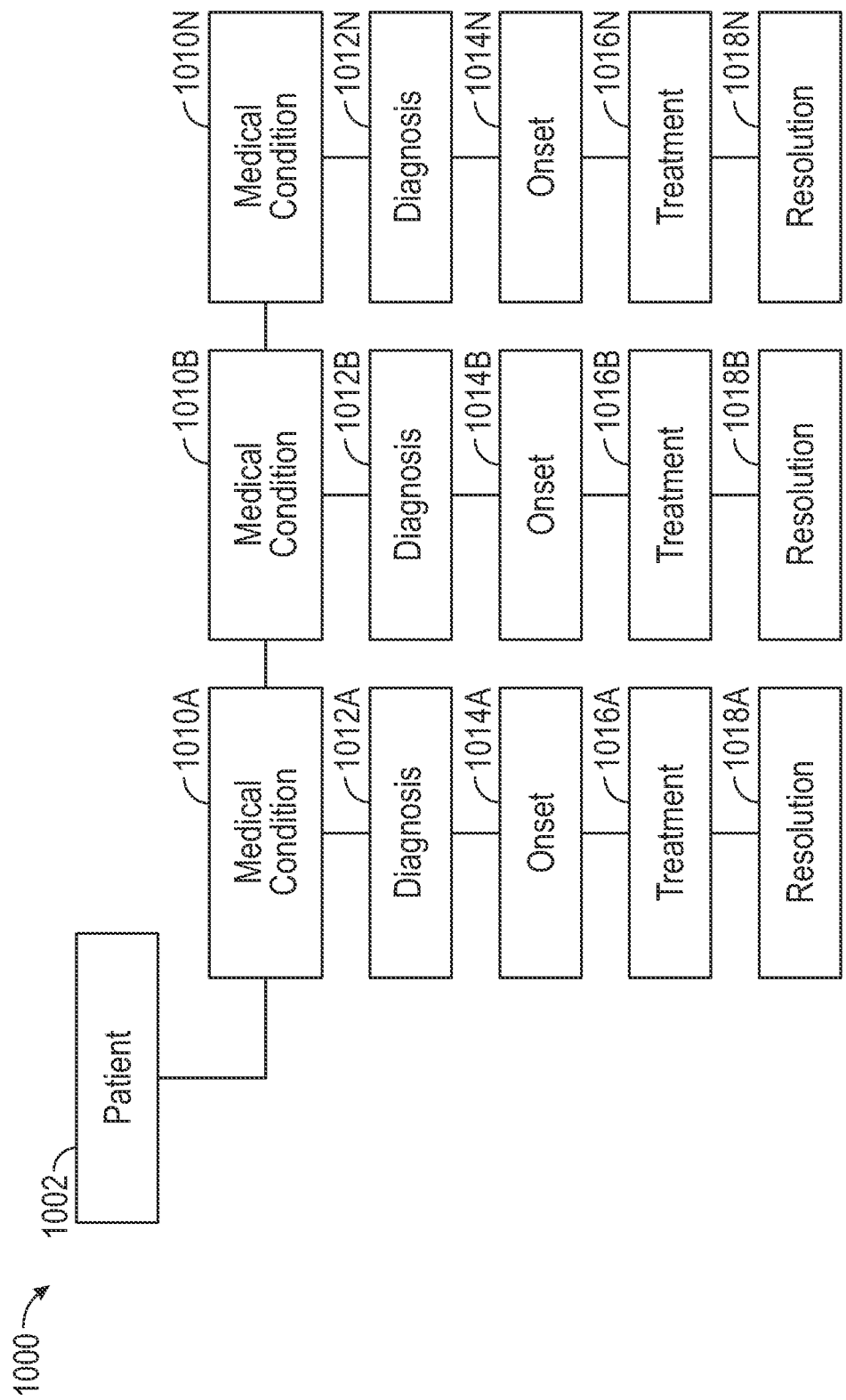
FIG. 10 depicts patient medical history for use in predicting wound care resources using an ML model, according to one embodiment.

FIG. 10 depicts patient medical history 1000 for use in predicting wound care resources using an ML model, according to one embodiment. In an embodiment, the patient medical history 1000 provide examples for the patient medical history 134, described above in relation to FIG. 1. A patient 1002 includes one or more medical conditions 1010A-N. Each medical condition includes a respective diagnosis 1012A-N, a respective onset description 1014A-N (e.g., a date or textual description), a respective treatment 1016A-N (e.g., a treatment history for the medical condition), and a respective resolution 1018A-N (e.g., a date of resolution or a notation that the medical condition is ongoing). These are merely examples, and each medical condition 1010A-N can include any suitable data. Further, the medical conditions 1010A-N are merely examples, and the patient 1002 can include any suitable medical history data.

Figure 11:
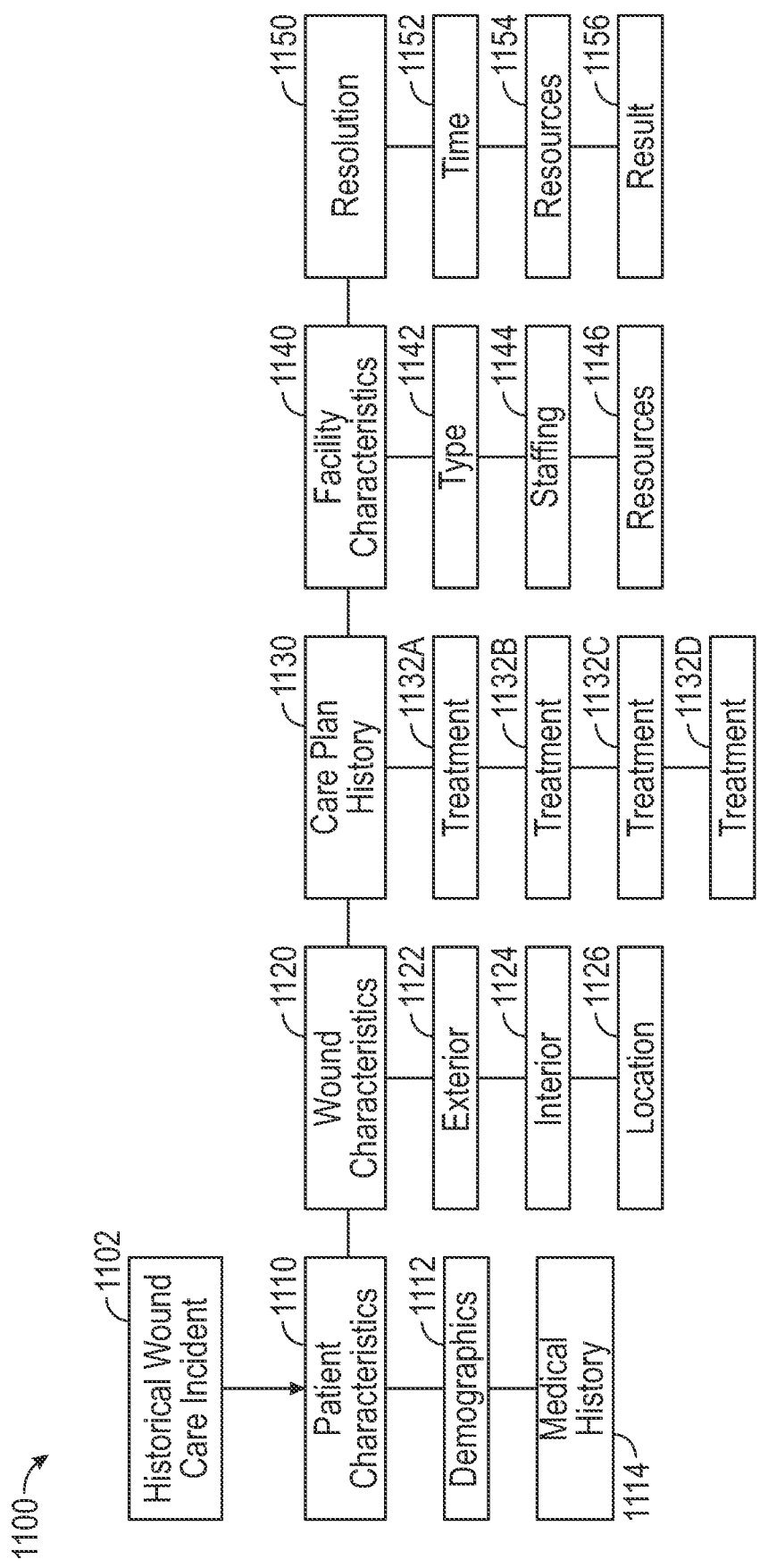
FIG. 11 depicts historical wound care incident data for use in predicting wound care resources using an ML model, according to one embodiment.

FIG. 11 depicts historical wound care incident data 1100 for use in predicting wound care resources using an ML model, according to one embodiment. In an embodiment, the historical wound care incident data 1100 provide examples for the historical wound care data 140, described above in relation to FIG. 1. Further, in an embodiment, the historical wound care incident data 1100 corresponds to any suitable patient (e.g., in addition to the patient for whom a wound is being treated). For example, the historical wound care incident data 1100 can be maintained by a healthcare provider (e.g., in a suitable anonymized or private format).

A historical wound care incident 1102 includes patient characteristics 1110. In an embodiment, the patient characteristics 1110 correspond with the patient characteristics 900 illustrated in FIG. 9 (e.g., for the patient with the historical wound). The patient characteristics 1110 include demographics 1112 (e.g., age, height, weight) and medical history 1114. These are merely examples, and the patient characteristics 1110 can include any suitable data.

The historical wound care incident 1102 further includes wound characteristics 1120. In an embodiment, the wound characteristics 1120 correspond with the wound characteristics 800 illustrated in FIG. 8 (e.g., for the relevant historical wound). The wound characteristics 1120 include exterior characteristics 1122 (e.g., size, color), interior characteristics 1124 (e.g., size, color, depth), and location 1126. These are merely examples, and the wound characteristics 1120 can include any suitable data.

The historical wound care incident 1102 further includes care plan history 1130. For example, the care plan history 1130 can describe one or more treatments 1132A-N used to treat the relevant wound. These are merely examples, and the care plan history 1130 can include any suitable data.

The historical wound care incident 1102 further includes one or more facility characteristics 1140 (e.g., describing any facilities used to treatment the wound, including outpatient and in-patient facilities). The facility characteristics 1140 include a type 1142 (e.g., in-patient, out-patient, or any other suitable type), staffing data 1144 (e.g., describing a number and type of staffing at the facility), and resources data 1146 (e.g., describing the available resources, including equipment, staffing, medication, and any other suitable resources). These are merely examples, and the facility characteristics 1140 can include any suitable data.

The historical wound care incident 1102 further includes a resolution 1150. For example, the resolution 1150 can include a time 1152 (e.g., a time of resolution), resources 1154 (e.g., equipment, staffing, and other resources used in resolution), and result 1156 (e.g., the end result of treatment). These are merely examples, and the resolution 1150 can include any suitable data. Further, the patient characteristics 1110, wound characteristics 1120, care plan history 1130, facility characteristics 1140, and resolution 1150, are merely examples. The historical wound care incident 1102 can include any suitable data.

Example of Training an ML Model for Predicting Wound Care Resources

Figure 12A:
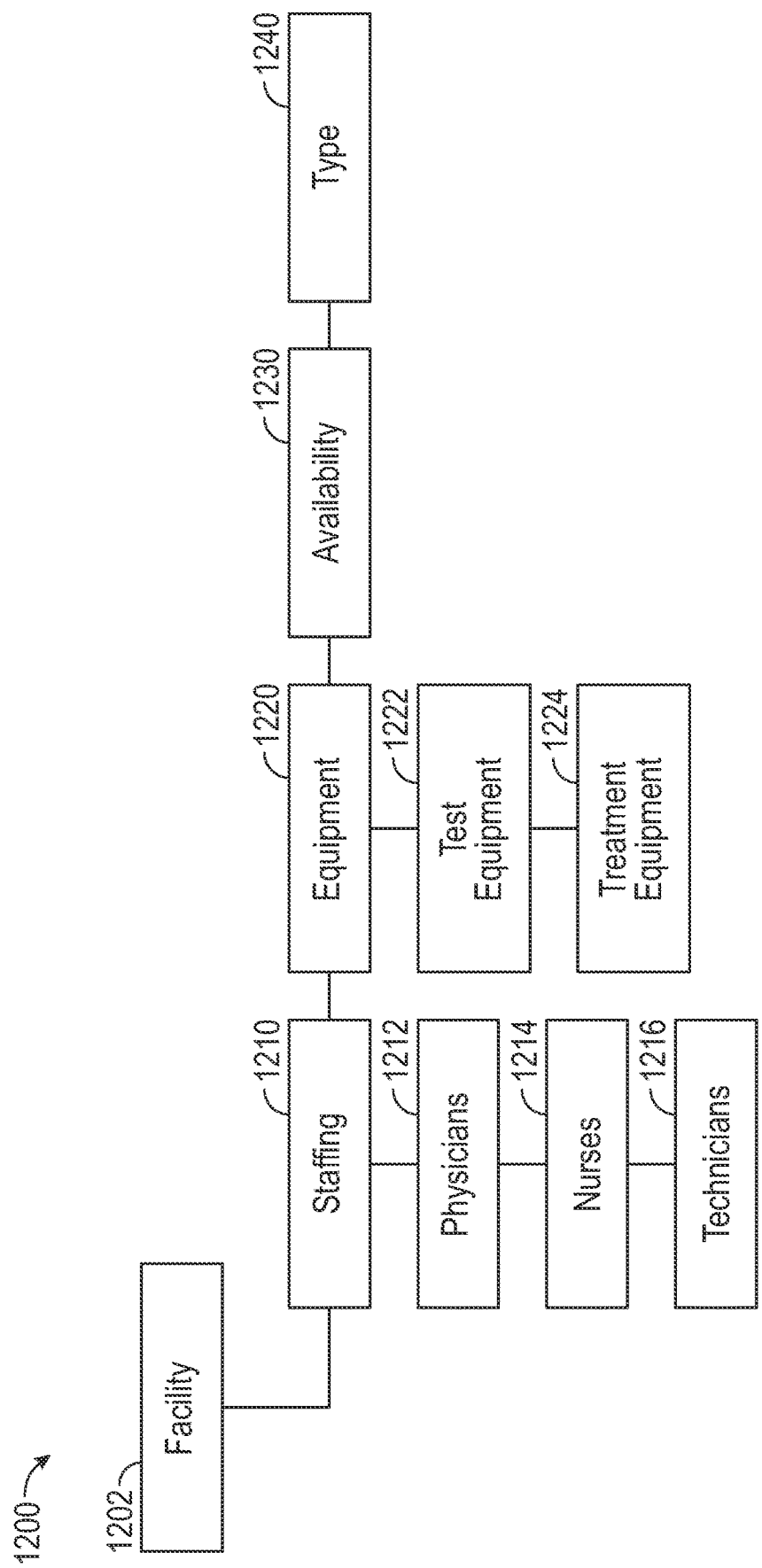
FIG. 12A depicts current facility data for use in predicting wound care resources using an ML model, according to one embodiment.

FIG. 12A depicts current facility data 1200 for use in predicting wound care resources using an ML model, according to one embodiment. A facility 1202 includes staffing data 1210 (e.g., describing staffing for the facility). The staffing data 1210 includes physicians 1212, nurses 1214, and technicians 1216. These are merely examples, and the staffing data 1210 can include any suitable data.

The facility 1202 further includes data describing one or more equipment items 1220. The equipment items can include, for example, test equipment 1222, treatment equipment 1224, and any other suitable equipment. The facility 1202 further includes availability data 1230, and type data 1240 (e.g., reflecting the type of facility). These are merely examples, and the equipment 1220, availability 1230, and type 1240 can include any suitable data. Further, the staffing data 1210, equipment data 1220, availability data 1230, and type data 1240, are merely examples. The facility 1202 can include any suitable data.

Figure 12B:
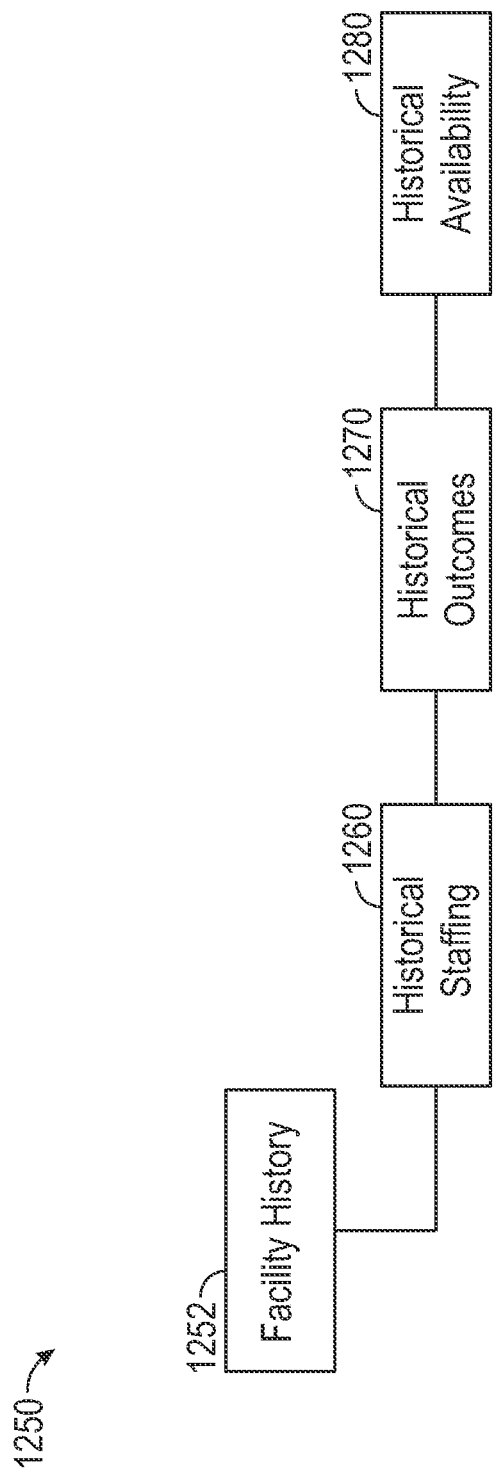
FIG. 12B depicts facility history data for use in predicting wound care resources using an ML model, according to one embodiment.

FIG. 12B depicts facility history data 1250 for use in predicting wound care resources using an ML model, according to one embodiment. A facility history 1252 (e.g., history data for a given facility) includes historical staffing data 1260. In an embodiment, this includes data describing historical staffing at the facility over a period of time (e.g., average staffing, peak staffing, minimum staffing, and any other suitable historical staffing data). The facility history further includes historical outcomes 1270 (e.g., reflecting historical patient treatment outcomes). The historical outcomes 1270 can reflect outcomes for wound treatment, for treatment generally, or both. The facility history 1252 further includes historical availability data 1280 (e.g., reflecting historical availability for patient treatment at the facility). These are merely examples, and the historical staffing 1260, historical outcomes 1270, and historical availability 1280 can include any suitable data. Further, the historical staffing 1260, historical outcomes 1270, and historical availability 1280, are merely examples. The facility history 1252 can include any suitable data.

Figure 13:
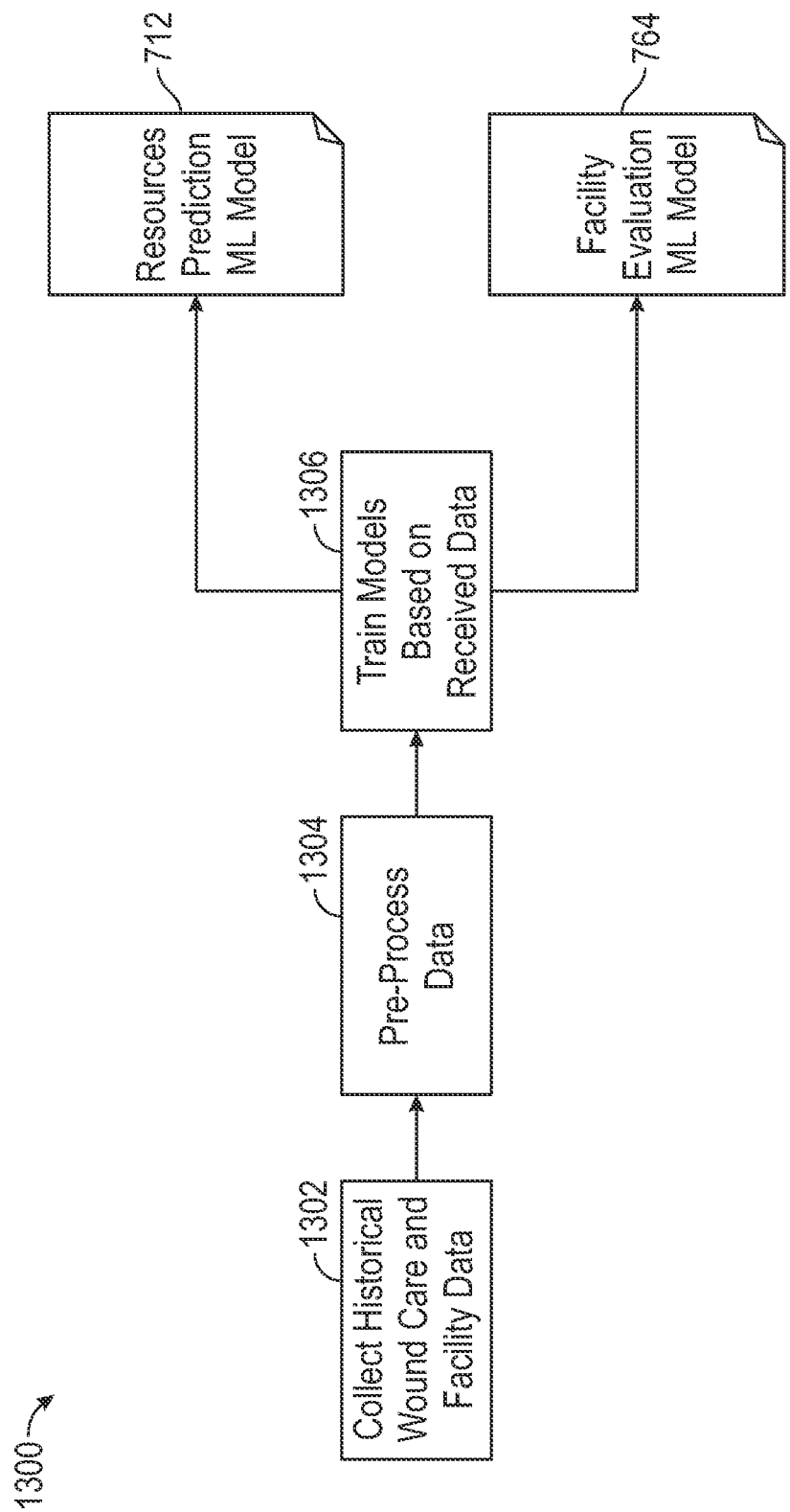
FIG. 13 is a flowchart illustrating training an ML model for predicting wound care resources using computer vision, according to one embodiment.

FIG. 13 is a flowchart 1300 illustrating training an ML model for predicting wound care resources using computer vision, according to one embodiment.

At block 1302, a training service (e.g., a human administrator or a software or hardware service) collects historical wound care data and historical facility data. For example, a wound prediction service (e.g., the wound prediction service 122 illustrated in FIGS. 1 and 2) can be configured to act as the training service and collect historical wound care data and historical facility data. This is merely an example, and any suitable software or hardware service can be used (e.g., a wound prediction training service).

At block 1304, the training service (or other suitable service) pre-processes the collected historical wound care and historical facility data. For example, the training service can create feature vectors reflecting the values of various features, for each historical wound and historical facility.

At block 1306, the training service trains the ML models using the feature vectors. For example, the training service can use feature vectors describing historical wound care and facility data to train the resources prediction ML model 712 (e.g., as discussed above in relation to FIG. 7A) to predict treatment resources. As another example, the training service can use feature vectors describing historical facility data to train the facility evaluation ML model 764 (e.g., as discussed above in relation to FIG. 7B) to generate a facility score. In an embodiment, the training service can further use historical facility score data to train the resources prediction ML model 712.

In an embodiment, the pre-processing and training can be done as batch training. In this embodiment, all data is pre-processed at once (e.g., all historical wound care and facility data), and provided to the training service at 1306. Alternatively, the pre-processing and training can be done in a streaming manner. In this embodiment, the data is streaming, and is continuously pre-processed and provided to the training service. For example, it can be desirable to take a streaming approach for scalability. The set of training data may be very large, so it may be desirable to pre-process the data, and provide it to the training service, in a streaming manner (e.g., to avoid computation and storage limitations).

Figure 14:
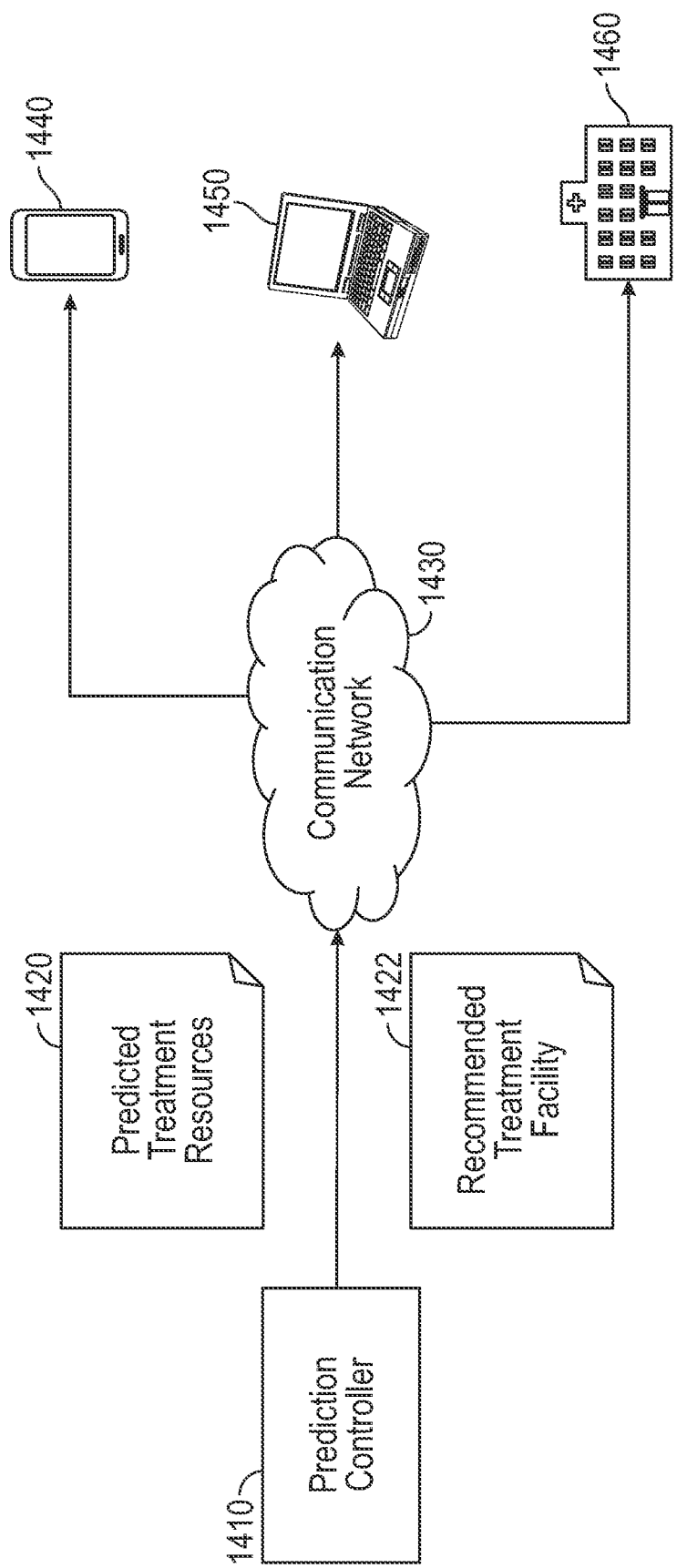
FIG. 14 depicts using predicted wound care resources, according to one embodiment.

FIG. 14 depicts using predicted wound care resources, according to one embodiment. In an embodiment, a prediction controller 1410 (e.g., the prediction controller 200 illustrated in FIG. 2) generates predicted treatment resources 1420, a recommended treatment facility 1422, or both. For example, as discussed above in relation to block 310 in FIG. 3 and FIG. 7A, a wound prediction service (e.g., the wound prediction service 122 illustrated in FIGS. 1-2) can use a wound prediction ML model (e.g., wound prediction ML model 124 illustrated in FIGS. 1-2) to predict necessary treatment resources and to predict a recommended treatment facility.

For example, the wound prediction service can use detected wound characteristics, generated using a wound detection service (e.g., the wound detection service 112 illustrated in FIG. 1) and a wound detection ML model (e.g., the wound detection ML model 114 illustrated in FIGS. 1-2) from captured sensor data (e.g., a captured image of the wound). As discussed above, FIG. 8 provides an example of wound characteristics. The wound prediction service can further use any, or all, of patient characteristics (e.g., as illustrated in FIG. 9), patient medical history (e.g., as illustrated in FIG. 10), historical wound care incidents (e.g., as illustrated in FIG. 11), and facility data (e.g., as illustrated in FIGS. 12A-B).

In an embodiment, the prediction controller 1410 transmits the predicted treatment resources 1420, the recommended treatment facility, or both over a communication network 1430 to any, or all, of a patient 1440, a care provider 1450, and a healthcare facility 1460. The communication network 1430 can be any suitable communication network, including the Internet, a wide area network, a local area network, or a cellular network, and can use any suitable wired or wireless communication technique (e.g., WiFi or cellular communication).

In an embodiment, any, or all, of the patient 1440, the care provider 1450, and the healthcare facility 1460 receive the predicted treatment resources 1420, the recommended treatment facility 1422, or both. The predicted treatment resources 1420 can then be used to treat the patient wound, or select treatment for the patient wound, and the recommended treatment facility 1422 can be used to select a treatment facility. For example, the patient 1440 can receive the predicted treatment resources 1420 and the recommended treatment facility 1422 at a suitable electronic device (e.g., a smartphone, tablet, laptop computer, desktop computer, or any other suitable device) and can use it to select or improve treatment (e.g., using a mobile application or local application running on the patient device, or accessing the predicted treatment resources 1420 and recommended treatment facility 1422 over the communication network 1430).

Similarly, the care provider 1450 or the healthcare facility 1460 (e.g., a healthcare professional at the healthcare facility 1460) can receive the predicted treatment resources 1420, the recommended treatment facility 1422, or both. The care provider or healthcare facility can use the predicted treatment resources 1420 to develop, or select, a treatment plan for the patient, and can use the recommended treatment facility to select a treatment facility for the patient.

Further, the care provider 1450 or healthcare facility 1460 can use the predicted treatment resources 1420 to ensure that sufficient resources and staffing are available for the patient. For example, the care provider 1450 or healthcare facility 1460 can use the predicted treatment resources 1420 to order necessary supplies, or equipment, to treat the patient. As another example, the care provider 1450 or healthcare facility 1460 can use the predicted treatment resources 1420 to schedule staffing to ensure that appropriate staffing is available to treat the patient.

In an embodiment, the prediction controller 1410 can interact directly with an inventory system to procure necessary resources or equipment. For example, the prediction controller 1410 can interact with an inventory system of a healthcare facility 1460 (e.g., using a suitable application programming interface (API), web interface, or other electronic interface) to place orders for supplies or equipment identified in the predicted treatment resources 1420. In an embodiment, these orders could be reviewed by a healthcare professional before being submitted, or could be submitted automatically. Similarly, the prediction controller 1410 can interact with an employee scheduling system of a healthcare facility 1460 (e.g., using a suitable API, web interface, or other electronic interface) to develop a schedule to meet staffing needs described in the predicted treatment resources 1420. In an embodiment, the proposed schedule could be reviewed by a healthcare professional before being submitted, or could be submitted automatically.

In an embodiment, any, or all, of patient 1440, the care provider 1450, and the healthcare facility 1460 store the predicted treatment resources 1420 and recommended treatment facility 1422. For example, this can allow the recipient to access the predicted treatment resources 1420 and recommended treatment facility 1422 without requiring a continuous network connection.

Figure 15:
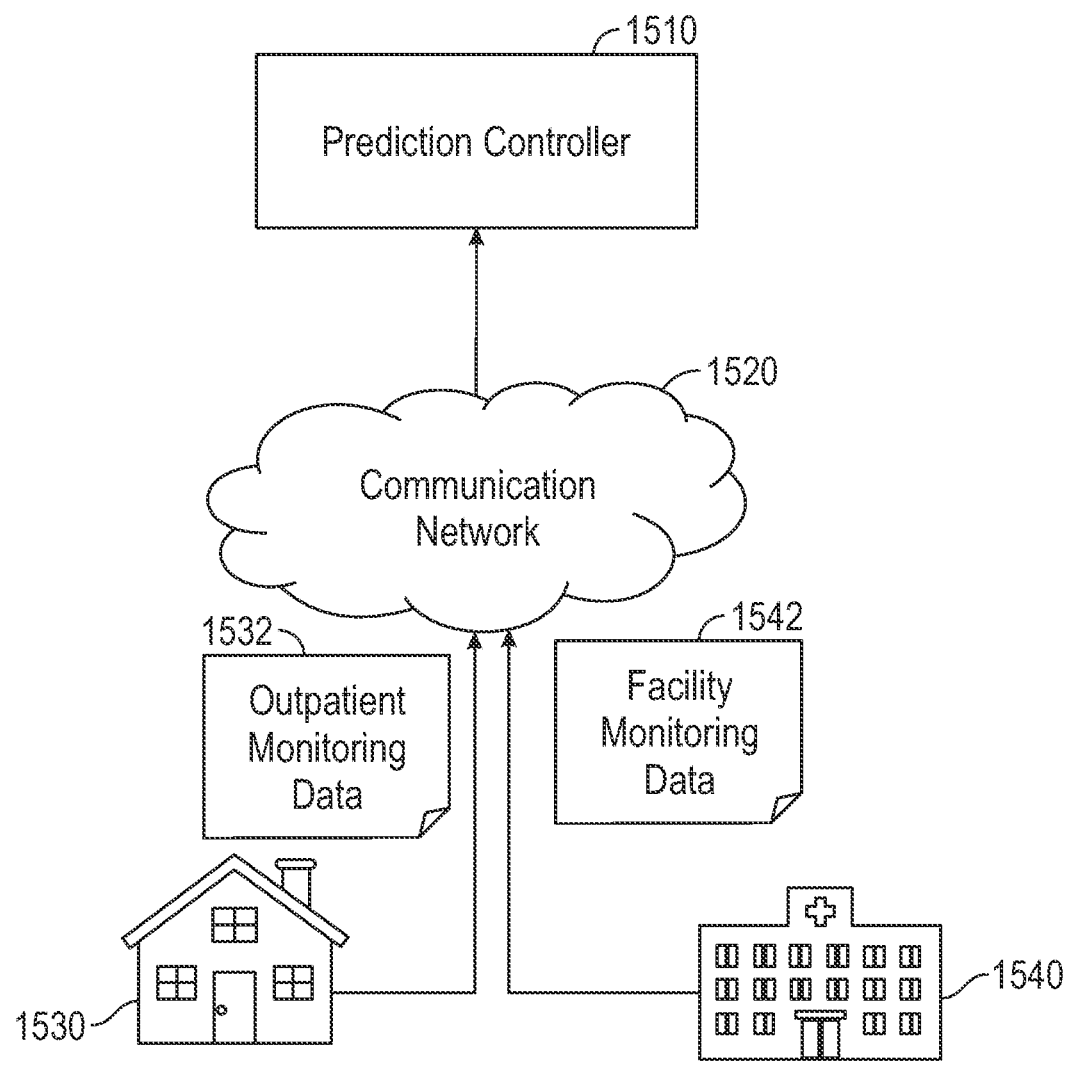
FIG. 15 depicts ongoing monitoring of patient care for predicting wound care resources, according to one embodiment.

FIG. 15 depicts ongoing monitoring of patient care for predicting wound care resources, according to one embodiment. As discussed above in relation to the ongoing patient monitoring data 170 illustrated in FIG. 1, in an embodiment the predicted wound care resources can be revised based on ongoing monitoring of the treatment progress for the patient's wound. In an embodiment, a patient is treated at an out-patient facility 1530. The out-patient facility 1530 continues to monitor treatment of the wound.

For example, the patient, or a care provider, can continue to capture electronic images of the wound as it is treated, or capture electronic sensor data during treatment. The patient, or care provider, can transmit this out-patient monitoring data 1532 (e.g., the captured image or other sensor data) to a prediction controller 1510 (e.g., the prediction controller 200 illustrated in FIG. 2) using a communication network 1520. The communication network 1520 can be any suitable communication network, including the Internet, a wide area network, a local area network, or a cellular network, and can use any suitable wired or wireless communication technique (e.g., WiFi or cellular communication).

In an embodiment, the prediction controller 1510 can use the out-patient monitoring data 1532 to revise the predicted wound care resources. For example, as discussed above in relation to FIG. 4, a computer vision service can use a computer vision ML model to identify wound characteristics from a captured wound image. These wound characteristics can then be used to predict wound care resources using a resources prediction ML model (e.g., as discussed above in relation to FIGS. 7A-B). The out-patient monitoring data 1532 can include one or more additional captured images of the wound, and a suitable computer vision ML model can be used to detect wound characteristics from these images. The prediction controller 1510 can then use the updated wound characteristics to predict updated wound care resources.

Alternatively, or in addition, the patient is treated at healthcare facility 1540. Just like at the out-patient facility 1530, the patient's wound can be continuously monitored at the healthcare facility 1540 (e.g., by a care provider or by the patient). The care provider, or patient, can transmit facility monitoring data 1542 (e.g., updated captured sensor data for the wound) to the prediction controller 1510 using the communication network 1520. The prediction controller 1510 can use the facility monitoring data 1542 to revise the predicted wound care resources. For example, as discussed above in relation to FIG. 4, a computer vision service can use a computer vision ML model to identify wound characteristics from a captured wound image. These wound characteristics can then be used to predict wound care resources using a resources prediction ML model (e.g., as discussed above in relation to FIGS. 7A-B). The facility monitoring data 1542 can include one or more additional captured images of the wound, and a suitable computer vision ML model can be used to detect wound characteristics from these images. The prediction controller 1510 can then use the updated wound characteristics to predict updated wound care resources.

Further, in an embodiment, the out-patient monitoring data 1532 and the facility monitoring data 1542 can be used to continuously train the resources prediction ML model. For example, out-patient monitoring data 1532 and the facility monitoring data 1542 can include additional captured images of the wound during treatment. The computer vision service can be used to identify characteristics of these wounds, and the prediction ML model can identify, from these characteristics, how treatment is progressing for the patient. This indication of progress, along with the previously predicted wound care resources, can be used as training data to further refine the resources prediction ML model.

Example Clauses

Implementation examples are described in the following numbered clauses:

Clause 1: A method, comprising: determining a plurality of characteristics of a wound for a patient based on an image of the wound, comprising: detecting the plurality of characteristics based on analyzing the image using a first machine learning (ML) model trained to detect wound characteristics from a captured image, and predicting at least one of: (i) treatment resources or (ii) a treatment facility for treating the wound, including: providing to a second trained ML model the plurality of characteristics of the wound, patient medical data for the patient, and treatment facility data describing a plurality of available treatment facilities.

Clause 2: The method of any of clauses 1 or 3-10, wherein the method comprises predicting the treatment facility for treating the wound, and wherein the plurality of available treatment facilities comprises one or more in-patient facilities and one or more out-patient facility options.

Clause 3: The method of any of clauses 1-2 or 4-10, further comprising: determining a plurality of facility treatment scores relating to the plurality of treatment facilities, and selecting the treatment facility, from among the plurality of available treatment facilities, based on the plurality of facility treatment scores.

Clause 4: The method of any of clauses 1-3 or 5-10, wherein determining the plurality of facility treatment scores comprises: providing the treatment facility data and facility history data relating to the plurality of treatment facilities to a third ML model, wherein the third ML model is trained to determine facility treatment scores based on treatment venue data and facility history data.

Clause 5: The method of any of clauses 1-4 or 6-10, wherein the method comprises predicting treatment resources, and wherein the treatment resources comprise at least one of: (i) staffing resources, (ii) equipment resources, or (iii) a predicted time for treatment.

Clause 6: The method of any of clauses 1-5 or 7-10, wherein the treatment resources comprise the predicted time for treatment.

Clause 7: The method of any of clauses 1-6 or 8-10, further comprising: identifying a prophylactic treatment task for the wound based on the plurality of characteristics of the wound, and transmitting an electronic alert relating to the treatment task.

Clause 8: The method of any of clauses 1-7 or 9-10, wherein identifying the prophylactic treatment task further comprises: transmitting the alert to a care provider for the patient electronically using a communication network, prior to completing the predicting the at least one of the treatment resources or a treatment facility for treating the wound.

Clause 9: The method of any of clauses 1-8 or 10, wherein detecting the plurality of characteristics of the wound further comprises: determining at least one of a depth, a color, or a size of the wound, based on the image of the wound.

Clause 10: The method of any of clauses 1-9, wherein the second trained ML model is trained using prior wound care outcome data comprising data reflecting wound characteristics, treatment, and resolution for each of a plurality of past wounds relating to a plurality of prior patients.

Clause 11: A processing system, comprising: a memory comprising computer-executable instructions; and one or more processors configured to execute the computer-executable instructions and cause the processing system to perform a method in accordance with any one of Clauses 1-10.

Clause 12: A processing system, comprising means for performing a method in accordance with any one of Clauses 1-10.

Clause 13: A non-transitory computer-readable medium comprising computer-executable instructions that, when executed by one or more processors of a processing system, cause the processing system to perform a method in accordance with any one of Clauses 1-10.

Clause 14: A computer program product embodied on a computer-readable storage medium comprising code for performing a method in accordance with any one of Clauses 1-10.

ADDITIONAL CONSIDERATIONS

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A method, comprising:
   determining a plurality of characteristics of a wound for a patient based on an image of the wound, comprising:
      detecting the plurality of characteristics based on analyzing the image using a first machine learning (ML) model trained to detect wound characteristics from a captured image, wherein the first ML model comprises a computer vision model;
   providing, to one or more second trained ML models, different from the first ML model, the plurality of characteristics of the wound, patient medical data for the patient, and treatment facility data describing a plurality of available treatment facilities to predict a resource prediction comprising:
      (i) treatment resources for treating the wound, and
      (ii) a treatment facility for treating the wound based at least in part on historical treatment outcomes for the treatment facility;
   transmitting the resource prediction to at least one of (i) the patient, (ii) a care provider of the patient, or (iii) the treatment facility, wherein the resource prediction is used to treat the wound of the patient; and
   based on the resource prediction, performing at least one of: (i) intake of the patient to the treatment facility, (ii) treatment of the patient at the treatment facility, or (iii) discharge of the patient for transfer to the treatment facility.

2. The method of claim 1, wherein the method comprises predicting the treatment facility for treating the wound, and wherein the plurality of available treatment facilities comprises one or more in-patient facilities and one or more out-patient facility options.

3. The method of claim 2, further comprising:
   determining a plurality of facility treatment scores relating to the plurality of treatment facilities; and
   selecting the treatment facility, from among the plurality of available treatment facilities, based on the plurality of facility treatment scores.

4. The method of claim 3, wherein determining the plurality of facility treatment scores comprises:
   providing the treatment facility data and facility history data relating to the plurality of treatment facilities to a third ML model,
   wherein the third ML model is trained to determine facility treatment scores based on treatment venue data and facility history data.

5. The method of claim 1, wherein the method comprises predicting treatment resources, and wherein the treatment resources comprise at least one of: (i) staffing resources, (ii) equipment resources, or (iii) a predicted time for treatment.

6. The method of claim 5, wherein the treatment resources comprise the predicted time for treatment.

7. The method of claim 1, further comprising:
   identifying a prophylactic treatment task for the wound based on the plurality of characteristics of the wound; and
   transmitting an electronic alert relating to the treatment task.

8. The method of claim 7, wherein identifying the prophylactic treatment task further comprises:
   transmitting the alert to a care provider for the patient electronically using a communication network, prior to completing the predicting the at least one of the treatment resources or a treatment facility for treating the wound.

9. The method of claim 1, wherein detecting the plurality of characteristics of the wound further comprises:
determining at least one of a depth, a color, or a size of the wound, based on the image of the wound.

10. The method of claim 1, wherein the second trained ML model is trained using prior wound care outcome data comprising data reflecting wound characteristics, treatment, and resolution for each of a plurality of past wounds relating to a plurality of prior patients.

11. An apparatus comprising:
a memory; and
a hardware processor communicatively coupled to the memory, the hardware processor configured to perform operations comprising:
  determining a plurality of characteristics of a wound for a patient based on an image of the wound, comprising:
    detecting the plurality of characteristics based on analyzing the image using a first machine learning (ML) model trained to detect wound characteristics from a captured image, wherein the first ML model comprises a computer vision model;
  providing, to one or more second trained ML models, different from the first ML model, the plurality of characteristics of the wound, patient medical data for the patient, and treatment facility data describing a plurality of available treatment facilities to predict a resource prediction comprising:
    (i) treatment resources for treating the wound, and
    (ii) a treatment facility for treating the wound based at least in part on historical treatment outcomes for the treatment; and
  transmitting the resource prediction to at least one of (i) the patient, (ii) a care provider of the patient, or (iii) the treatment facility, wherein the resource prediction is used to treat the wound of the patient; and
  based on the resource prediction, performing at least one of: (i) intake of the patient to the treatment facility, (ii) treatment of the patient at the treatment facility, or (iii) discharge of the patient for transfer to the treatment facility.

12. The apparatus of claim 11 wherein the operations comprise predicting the treatment facility for treating the wound, and wherein the plurality of available treatment facilities comprises one or more in-patient facilities and one or more out-patient facility options.

13. The apparatus of claim 12, the operations further comprising:
determining a plurality of facility treatment scores relating to the plurality of treatment facilities; and
selecting the treatment facility, from among the plurality of available treatment facilities, based on the plurality of facility treatment scores.

14. The apparatus of claim 13, wherein determining the plurality of facility treatment scores comprises:
providing the treatment facility data and facility history data relating to the plurality of treatment facilities to a third ML model,
wherein the third ML model is trained to determine facility treatment scores based on treatment venue data and facility history data.

15. The apparatus of claim 11, wherein the operations comprise predicting a time for treatment.

16. The apparatus of claim 11, the operations further comprising:
identifying a prophylactic treatment task for the wound based on the plurality of characteristics of the wound; and
transmitting an electronic alert relating to the treatment task to a care provider for the patient electronically using a communication network, prior to completing the predicting the at least one of the treatment resources or a treatment facility for treating the wound.

17. A non-transitory computer-readable medium comprising instructions that, when executed by a processor, cause the processor to perform operations comprising:
determining a plurality of characteristics of a wound for a patient based on an image of the wound, comprising:
  detecting the plurality of characteristics based on analyzing the image using a first machine learning (ML) model trained to detect wound characteristics from a captured image, wherein the first ML model comprises a computer vision model;
providing, to one or more second trained ML models, different from the first ML model, the plurality of characteristics of the wound, patient medical data for the patient, and treatment facility data describing a plurality of available treatment facilities to predict a resource prediction comprising:
  (i) treatment resources for treating the wound, and
  (ii) a treatment facility for treating the wound based at least in part on historical treatment outcomes for the treatment; and
transmitting the resource prediction to at least one of (i) the patient, (ii) a care provider of the patient, or (iii) the treatment facility, wherein the resource prediction is used to treat the wound of the patient; and
based on the resource prediction, performing at least one of: (i) intake of the patient to the treatment facility, (ii) treatment of the patient at the treatment facility, or (iii) discharge of the patient for transfer to the treatment facility.

18. The non-transitory computer-readable medium of claim 17 wherein the operations comprise predicting the treatment facility for treating the wound, and wherein the plurality of available treatment facilities comprises one or more in-patient facilities and one or more out-patient facility options.

19. The non-transitory computer-readable medium of claim 18, the operations further comprising:
determining a plurality of facility treatment scores relating to the plurality of treatment facilities, comprising:
  the treatment facility data and facility history data relating to the plurality of treatment facilities to a third ML model,
  wherein the third ML model is trained to determine facility treatment scores based on treatment venue data and facility history data; and
selecting the treatment facility, from among the plurality of available treatment facilities, based on the plurality of facility treatment scores.

20. The non-transitory computer-readable medium of claim 17, wherein the operations comprise predicting a time for treatment.

* * * * *